(12) United States Patent
Kaji et al.

(10) Patent No.: US 12,343,115 B2
(45) Date of Patent: Jul. 1, 2025

(54) DATA PROCESSING APPARATUS AND DATA PROCESSING METHOD

(71) Applicant: J. MORITA MFG. CORP., Kyoto (JP)

(72) Inventors: Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 175 days.

(21) Appl. No.: 18/190,003

(22) Filed: Mar. 24, 2023

(65) Prior Publication Data
US 2023/0301521 A1  Sep. 28, 2023

(30) Foreign Application Priority Data
Mar. 25, 2022  (JP) .................. 2022-050078

(51) Int. Cl.
*A61B 5/00* (2006.01)
*G06T 7/521* (2017.01)

(52) U.S. Cl.
CPC ............ *A61B 5/0088* (2013.01); *G06T 7/521* (2017.01); *G06T 2207/10* (2013.01)

(58) Field of Classification Search
CPC .............. A61B 5/0088; G06T 7/521; G06T 2207/20084; G06T 2207/30036; G06T 7/73; G06T 2207/10028; G06T 7/12; G06V 10/82; G06V 2201/03
See application file for complete search history.

(56) References Cited

U.S. PATENT DOCUMENTS

| 6,885,464 | B1 | 4/2005 | Pfeiffer et al. |
| 2014/0272774 | A1 | 9/2014 | Dillon et al. |
| 2015/0029309 | A1* | 1/2015 | Michaeli ............... G01B 11/25 348/46 |
| 2019/0147648 | A1 | 5/2019 | Wolff |

(Continued)

FOREIGN PATENT DOCUMENTS

| JP | 2000-74635 A | 3/2000 |
| JP | 2020-151008 A | 9/2020 |

(Continued)

OTHER PUBLICATIONS

Definition of outline, Nov. 9, 2024, Online Cambridge English Dictionary, ht tps://dictionary.cambridge.org/us/dictionary/english/outline, one page. (Year: 2024).*

(Continued)

*Primary Examiner* — Jeffery A Brier
(74) *Attorney, Agent, or Firm* — Oblon, McClelland, Maier & Neustadt, L.L.P.

(57) ABSTRACT

A data processing apparatus that includes an input interface to which three-dimensional data including position information of each point of a point group indicating a surface of at least one object is input; and processing circuitry that is configured to process the three-dimensional data that is input from the input interface. The processing circuitry is configured to process two-dimensional data from the three-dimensional data, identify a predetermined object among the at least one object based on the two-dimensional data, and extract predetermined three-dimensional data including the position information of each point of a point group indicating a surface of the predetermined object that is identified.

20 Claims, 16 Drawing Sheets

(56) References Cited

U.S. PATENT DOCUMENTS

| | | | |
|---|---|---|---|
| 2019/0150825 | A1 | 5/2019 | Kambara |
| 2020/0170760 | A1 | 6/2020 | Dawood |
| 2020/0281702 | A1 | 9/2020 | Kopelman et al. |
| 2020/0297187 | A1 | 9/2020 | Wakazome |
| 2020/0376769 | A1 | 12/2020 | Murphy et al. |
| 2021/0212806 | A1* | 7/2021 | Sorimoto ........... A61B 1/00096 |
| 2021/0217189 | A1* | 7/2021 | Sorimoto ................. G06T 7/55 |

FOREIGN PATENT DOCUMENTS

| | | | |
|---|---|---|---|
| JP | 2020-531960 A | 11/2020 | |
| JP | 2021-53174 A | 4/2021 | |
| WO | WO-2016012824 A1 * | 1/2016 | ............. A61B 5/107 |

OTHER PUBLICATIONS

Definition of outline, Nov. 9, 2024, Online Merriam-Webster, https://www.merriam-webster.com/dictionary/outline, one page. (Year: 2024).*

Office Action issued Apr. 4, 2023, in corresponding Japanese Patent Application No. 2022-101215 (with English Translation), 6 pages.

Yusuke Moriyama, et al., Evaluation of Dental Image Augmentation for the Severity Assessment of Periodontal Disease, 2019 International Conference on Computational Science and Computational Intelligence (CSCI), IEEE, 2019, pp. 924-929. (6 pgs.).

Office Action issued Jun. 14, 2022, in JP application No. 2022-050078, filed on Mar. 25, 2022, (w/English translation) (8 pgs).

Extended European Search Report issued Sep. 5, 2023, in corresponding European Patent Application No. 23162935.3, 7 pages.

* cited by examiner

FIG.10

| | THREE-DIMENSIONAL DATA THAT IS INPUT | | | | |
|---|---|---|---|---|---|
| | POSITION INFORMATION | | | NORMAL LINE INFORMATION | |
| X-COORDINATE | Y-COORDINATE | Z-COORDINATE | X-COMPONENT | Y-COMPONENT | Z-COMPONENT |
| 7.589479 | 17.008148 | 0.257312 | 0.032430 | -0.754360 | 0.655659 |
| 7.455763 | 17.083626 | 0.282419 | -0.261376 | -0.616214 | 0.742942 |
| 6.644024 | 18.460928 | 0.738178 | 0.358605 | -0.045641 | 0.932373 |
| 6.723327 | 18.086802 | 0.647297 | 0.322765 | -0.050151 | 0.945149 |
| 6.428038 | 18.072901 | 0.758502 | 0.312541 | -0.090993 | 0.945536 |
| 7.033796 | 17.053980 | 0.069908 | -0.328198 | -0.732382 | 0.596576 |
| 6.269164 | 18.153204 | 0.830183 | 0.311766 | -0.113734 | 0.943327 |
| 6.357689 | 17.824369 | 0.743043 | 0.185743 | -0.344547 | 0.920210 |
| 7.254097 | 16.402849 | -0.834512 | -0.278497 | -0.865927 | 0.415463 |
| 5.788676 | 18.057125 | 0.936171 | 0.167980 | -0.201836 | 0.964907 |
| 6.383657 | 17.710402 | 0.645624 | 0.094659 | -0.782029 | 0.616012 |
| 6.461415 | 17.617271 | 0.555074 | -0.017997 | -0.804334 | 0.593906 |
| 5.925761 | 18.151102 | 0.939822 | 0.237253 | -0.125757 | 0.963274 |
| 6.248242 | 17.277231 | -0.056271 | -0.197127 | -0.872989 | 0.446129 |
| 5.260770 | 17.556486 | 0.357177 | -0.011785 | -0.904845 | 0.425578 |
| 5.250275 | 17.739592 | 0.765335 | -0.001318 | -0.889364 | 0.457199 |
| 5.378457 | 17.316980 | -0.170421 | -0.033097 | -0.909505 | 0.414374 |
| 5.391177 | 17.460012 | 0.159294 | -0.024939 | -0.914875 | 0.402965 |
| 4.880158 | 17.801937 | 0.876624 | -0.004048 | -0.846091 | 0.533024 |
| 3.903229 | 18.019154 | 1.271811 | 0.087388 | -0.542954 | 0.835203 |
| ... | ... | ... | ... | ... | ... |

ONE SCAN

FIG.11

| | TRAINING DATA | |
|---|---|---|
| POSITION INFORMATION | | GROUND TRUTH LABEL |
| X-COORDINATE | Y-COORDINATE | |
| 7.589479 | 17.008148 | 01.000000 TONGUE |
| 7.455763 | 17.083626 | 01.000000 |
| 6.644024 | 18.460928 | 01.000000 |
| 6.723327 | 18.086802 | 02.000000 |
| 6.428038 | 18.072901 | 02.000000 |
| 7.033796 | 17.053980 | 02.000000 |
| 6.269164 | 18.153204 | 02.000000 |
| 6.357689 | 17.824369 | 02.000000 |
| 7.254097 | 16.402849 | 02.000000 |
| 5.788676 | 18.057125 | 02.000000 |
| 6.383657 | 17.710402 | 38.000000 LOWER JAW LEFT THIRD MOLAR |
| 6.461415 | 17.617271 | 38.000000 |
| 5.925761 | 18.151102 | 37.000000 LOWER JAW LEFT SECOND MOLAR |
| 6.248242 | 17.277231 | 37.000000 |
| 5.260770 | 17.556486 | 36.000000 |
| 5.250275 | 17.739592 | 36.000000 |
| 5.378457 | 17.316980 | 04.000000 FINGER |
| 5.391177 | 17.460012 | 51.000000 |
| 4.880158 | 17.801937 | 51.000000 |
| 3.903229 | 18.019154 | 51.000000 |
| ... | ... | ... |

ONE SCAN

FIG.12

| OBJECT | | | GROUND TRUTH LABEL |
|---|---|---|---|
| LOWER JAW | | TONGUE | 01 |
| | | LOWER JAW FIRST GAP (FRENUM) | 02 |
| | TOOTH ROW | LEFT CENTRAL INCISOR | 31 |
| | | LEFT LATERAL INCISOR | 32 |
| | | LEFT CANINE | 33 |
| | | LEFT FIRST PREMOLAR | 34 |
| | | LEFT SECOND PREMOLAR | 35 |
| | | LEFT FIRST MOLAR | 36 |
| | | LEFT SECOND MOLAR | 37 |
| | | LEFT THIRD MOLAR | 38 |
| | | RIGHT CENTRAL INCISOR | 41 |
| | | RIGHT LATERAL INCISOR | 42 |
| | | RIGHT CANINE | 43 |
| | | RIGHT FIRST PREMOLAR | 44 |
| | | RIGHT SECOND PREMOLAR | 45 |
| | | RIGHT FIRST MOLAR | 46 |
| | | RIGHT SECOND MOLAR | 47 |
| | | RIGHT THIRD MOLAR | 48 |
| | | LOWER JAW SECOND GAP (FRENUM) | 04 |
| | | LOWER LIP | 05 |
| UPPER JAW | | HARD PALATE | 06 |
| | | UPPER JAW FIRST GAP (FRENUM) | 07 |
| | TOOTH ROW | LEFT CENTRAL INCISOR | 21 |
| | | LEFT LATERAL INCISOR | 22 |
| | | LEFT CANINE | 23 |
| | | LEFT FIRST PREMOLAR | 24 |
| | | LEFT SECOND PREMOLAR | 25 |
| | | LEFT FIRST MOLAR | 26 |
| | | LEFT SECOND MOLAR | 27 |
| | | LEFT THIRD MOLAR | 28 |
| | | RIGHT CENTRAL INCISOR | 11 |
| | | RIGHT LATERAL INCISOR | 12 |
| | | RIGHT CANINE | 13 |
| | | RIGHT FIRST PREMOLAR | 14 |
| | | RIGHT SECOND PREMOLAR | 15 |
| | | RIGHT FIRST MOLAR | 16 |
| | | RIGHT SECOND MOLAR | 17 |
| | | RIGHT THIRD MOLAR | 18 |
| | | UPPER JAW SECOND GAP (FRENUM) | 09 |
| | | UPPER LIP | 10 |
| INSERTION OBJECT | | FINGER | 51 |
| | | TREATMENT INSTRUMENT | 52 |

FIG.13

COMBINED DATA AFTER REMOVAL OF UNNECESSARY OBJECT

| | POSITION INFORMATION | | | NORMAL LINE INFORMATION | | | IDENTIFICATION RESULT | REMOVE FLAG |
|---|---|---|---|---|---|---|---|---|
| X-COORDINATE | Y-COORDINATE | Z-COORDINATE | X-COMPONENT | Y-COMPONENT | Z-COMPONENT | | | |
| 7.589479 | 17.008148 | 0.257312 | 0.032430 | -0.754360 | 0.655659 | 01.000000 | 01.000000 |
| 7.455763 | 17.083626 | 0.282419 | -0.261376 | -0.616214 | 0.7... | 01.000000 | 01.000000 |
| 6.644024 | 18.460928 | 0.738178 | 0.358605 | -0.045641 | 0.9 TONGUE | 01.000000 | 01.000000 |
| ... | ... | ... | ... | ... | ... | ... | ... |
| 4.880158 | 17.801937 | 0.876624 | -0.004048 | -0.846091 | 0.533024 | 51.000000 | 01.000000 |
| 3.903229 | 18.019154 | 1.271811 | 0.087388 | -0.542954 | 0.83... FINGER | 51.000000 | 01.000000 |
| 6.357689 | 17.824369 | 0.743043 | 0.185743 | -0.344547 | 0.92... | 02.000000 | 00.000000 |
| 7.254097 | 16.402849 | -0.834512 | -0.278497 | -0.865927 | 0.415463 | 02.000000 | 00.000000 |
| 5.788676 | 18.057125 | 0.936171 | 0.167980 | -0.201836 | 0.964907 | 38.000000 | 00.000000 |
| 6.383657 | 17.710402 | 0.645624 | 0.094659 | -0.782029 | 0.616012 | 38.000000 | 00.000000 |
| 6.461415 | 17.617271 | 0.555074 | -0.017997 | -0.804334 | 0.593906 | 37.000000 | 00.000000 |
| 5.925761 | 18.151102 | 0.939822 | 0.237253 | -0.125757 | 0.963274 | 37.000000 | 00.000000 |
| 5.260770 | 17.556486 | 0.357177 | -0.011785 | -0.904845 | 0.425578 | 04.000000 | 00.000000 |
| 5.250275 | 17.739592 | 0.765335 | -0.0001318 | -0.889364 | 0.457199 | 04.000000 | 00.000000 |
| 5.378457 | 17.316980 | -0.170421 | -0.033097 | -0.909505 | 0.414374 | 04.000000 | 00.000000 |
| 5.391177 | 17.460012 | 0.159294 | -0.024939 | -0.914875 | 0.402965 | 36.000000 | 00.000000 |
| 4.880158 | 17.801937 | 0.876624 | -0.004048 | -0.846091 | 0.533024 | 36.000000 | 00.000000 |
| 3.903229 | 18.019154 | 1.271811 | 0.087388 | -0.542954 | 0.835203 | 36.000000 | 00.000000 |
| ... | ... | ... | ... | ... | ... | ... | ... |

ONE SCAN / ONE SCAN / ONE SCAN

DATA PROCESSING APPARATUS AND DATA PROCESSING METHOD

BACKGROUND OF THE DISCLOSURE

Field of the Disclosure

The present disclosure relates to a data processing apparatus and a data processing method for processing data including position information of at least one object inside a mouth.

Description of the Background Art

Conventionally, in a dental field, a technique is known according to which three-dimensional data of an object such as a tooth is acquired by scanning the inside of a mouth by a three-dimensional scanner. For example, Japanese Patent Publication No. 2000-74635 discloses a method of recording the shape of a tooth by capturing the tooth using a three-dimensional scanner.

SUMMARY

With the method disclosed in Japanese Patent Publication No. 2000-74635, a user is able to measure a tooth inside a mouth by using a three-dimensional image that is generated based on three-dimensional data acquired by the three-dimensional scanner, and is able to identify a type of the tooth that is measured, based on his/her knowledge, by checking the three-dimensional image showing the tooth. However, there is a demand for a technique that enables appropriate extraction of three-dimensional data of a predetermined object inside a mouth, such as a tooth, without requiring the user himself/herself to identify the predetermined object inside the mouth.

The present disclosure has been made to solve such a problem, and is aimed at providing a technique for easily and appropriately extracting three-dimensional data of a predetermined object inside a mouth.

According to an example of the present disclosure, there is provided a data processing apparatus for processing data including position information of at least one object inside a mouth. The data processing apparatus includes an input interface to which three-dimensional data including position information of each point of a point group indicating a surface of the at least one object is input; and processing circuitry that processes the three-dimensional data that is input from the input interface. The processing circuitry generates two-dimensional data from the three-dimensional data, identifies a predetermined object among the at least one object, based on the two-dimensional data, and extracts predetermined three-dimensional data including the position information of each point of a point group indicating a surface of the predetermined object that is identified.

According to an example of the present disclosure, there is provided a data processing method, of a computer, of processing data including position information of at least one object inside a mouth. The data processing method includes, as processes that are performed by the computer, receiving three-dimensional data including position information of each point of a point group indicating a surface of the at least one object; and processing the three-dimensional data that is received. The processing includes generating two-dimensional data from the three-dimensional data, identifying a predetermined object among the at least one object, based on the two-dimensional data, and extracting predetermined three-dimensional data including the position information of each point of a point group indicating a surface of the predetermined object that is identified.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 10 is a diagram for describing three-dimensional data that is input to the data processing apparatus according to the first embodiment;

FIG. 11 is a diagram for describing training data that is used at a time of machine learning of an estimation model according to the first embodiment;

FIG. 12 is a diagram for describing a correspondence relationship between each of a plurality of objects and a ground truth label;

FIG. 13 is a diagram for describing combined data after removal of an unnecessary object, generated by the data processing apparatus according to the first embodiment;

DETAILED DESCRIPTION

First Embodiment

Figure 1:
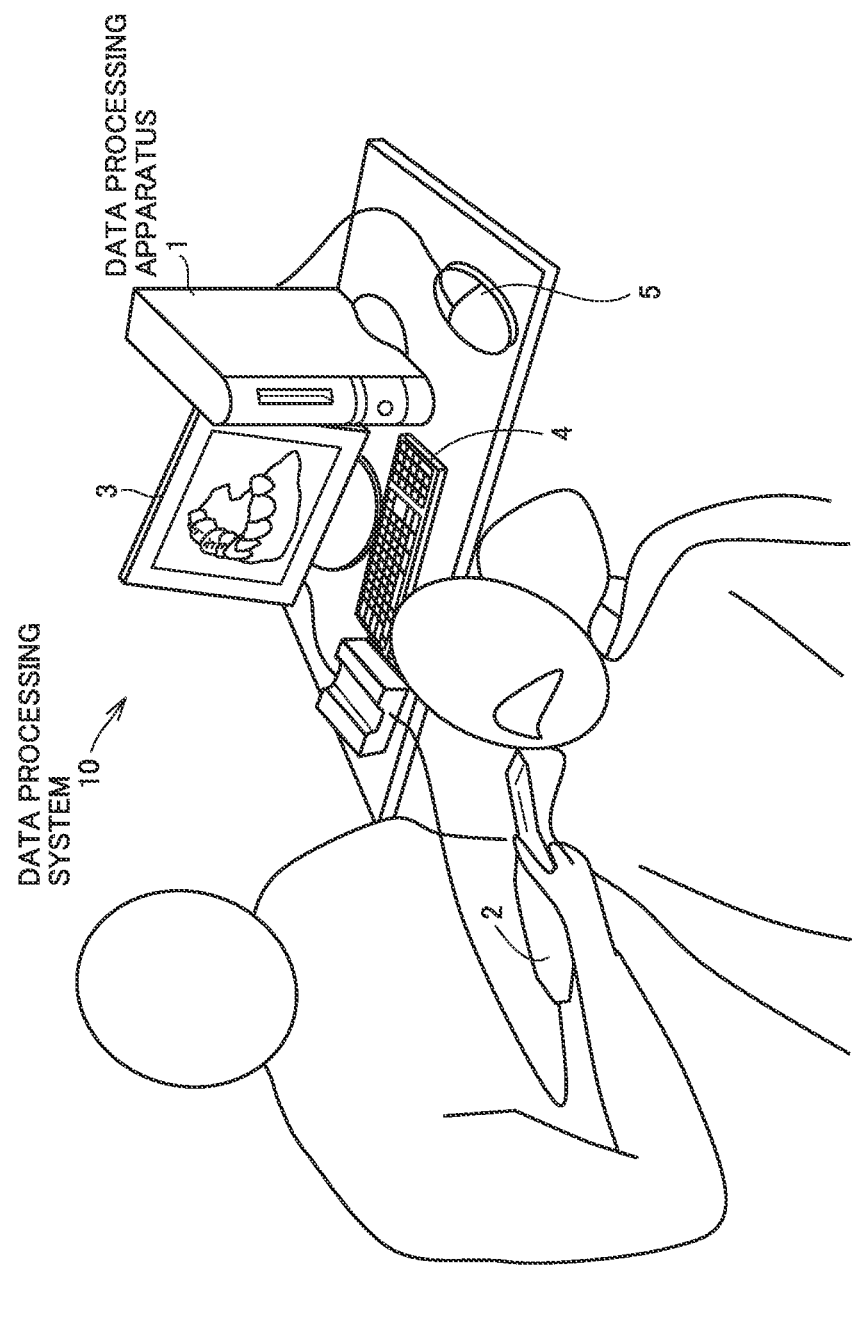
FIG. 1 is a diagram showing an example application of a data processing system and a data processing apparatus according to a first embodiment.

With reference to drawings, a first embodiment of the present disclosure will be described in detail. Additionally, same or corresponding parts in the drawings will be denoted by a same reference sign, and description thereof will not be repeated. [Example Application]

With reference to FIG. 1, an application example of a data processing system 10 and a data processing apparatus 1 according to the first embodiment will be described. FIG. 1 is a diagram showing an example application of data processing system 10 and data processing apparatus 1 according to the first embodiment.

As shown in FIG. 1, a user is able to acquire three-dimensional data of a plurality of objects inside a mouth of a target person, by scanning inside of the mouth using a three-dimensional scanner 2. The "user" may be any person who is to acquire the three-dimensional data of an object such as a tooth using three-dimensional scanner 2, such as a surgeon such as a dentist, a dental assistant, a professor or a student at a dental college, a dental technician, a technician at a manufacturer, or a worker at a manufacturing facility. The "target person" may be any person who is a potential scan target of three-dimensional scanner 2, such as a patient at a dental clinic or a test subject at a dental college. The "object" may be anything that is a potential scan target of three-dimensional scanner 2, such as a tooth inside the mouth of the target person.

Data processing system 10 includes data processing apparatus 1 and three-dimensional scanner 2. A display 3, a keyboard 4, and a mouse 5 are connected to data processing apparatus 1.

Three-dimensional scanner 2 is an image capturing apparatus that captures inside of a mouth, and acquires three-dimensional data of an object by a built-in three-dimensional camera. More specifically, by scanning the inside of a mouth, three-dimensional scanner 2 acquires, as the three-dimensional data, position information (coordinates on axes in a vertical direction, a horizontal direction, and a height direction) of each point of a point group (a plurality of points) indicating a surface of an object, by using an optical sensor or the like. That is, the three-dimensional data is position data including the position information of a position of each point of a point group forming the surface of an object.

Because a measurement range that three-dimensional scanner 2 is able to measure at one time is limited, in the case where the user desires to acquire the three-dimensional data of an entire tooth row (dental arch) inside a mouth, the user scans the inside of the mouth a plurality of times by moving and operating three-dimensional scanner 2 inside the mouth along the tooth row.

Data processing apparatus 1 generates two-dimensional image data corresponding to a two-dimensional image as seen from an unspecified point of view, based on the three-dimensional data acquired by three-dimensional scanner 2, and causes display 3 to display the two-dimensional image that is generated, and may thus make the user view a two-dimensional projection view of the surface of an object that is seen from a specific direction.

Furthermore, data processing apparatus 1 outputs the three-dimensional data to a dental laboratory. In the dental laboratory, a dental technician creates a dental model such as a dental prosthesis based on the three-dimensional data acquired from data processing apparatus 1. Additionally, in the case where an automatic manufacturing apparatus that is capable of automatically manufacturing the dental model, such as a milling machine or a 3D printer, is installed in a dental clinic, data processing apparatus 1 may output the three-dimensional data to the automatic manufacturing apparatus.

[Hardware Configuration of Data Processing Apparatus]

Figure 2:
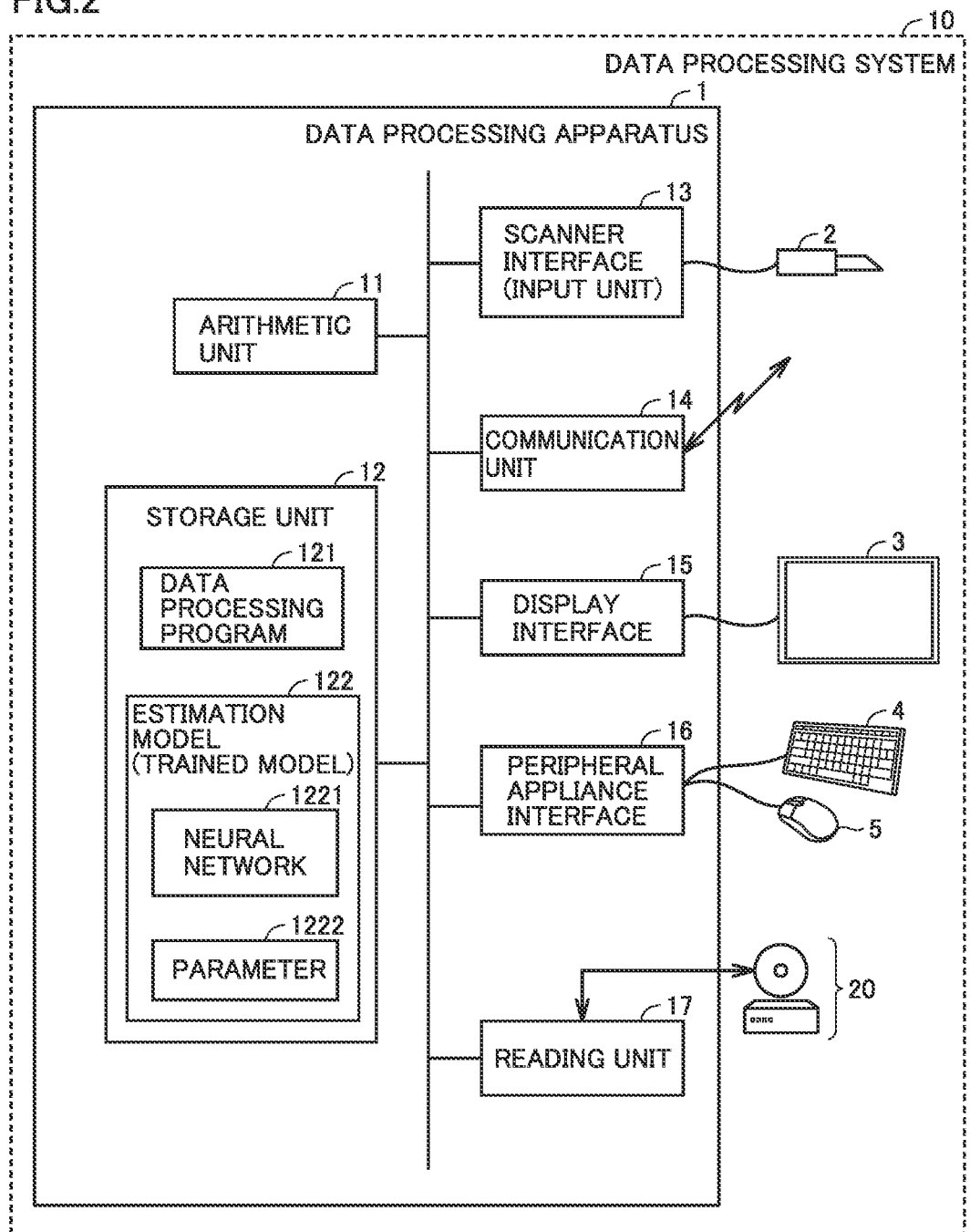
FIG. 2 is a block diagram showing a hardware configuration of the data processing apparatus according to the first embodiment.

With reference to FIG. 2, a hardware configuration of data processing apparatus 1 according to the first embodiment will be described. FIG. 2 is a block diagram showing the hardware configuration of data processing apparatus 1 according to the first embodiment. For example, data processing apparatus 1 may be implemented by a general-purpose computer, or may be implemented by a computer dedicated to data processing system 10.

As shown in FIG. 2, data processing apparatus 1 includes, as main hardware elements, an arithmetic unit 11, a storage unit 12, a scanner interface (input interface) 13, a communication unit 14, a display interface 15, a peripheral appliance interface 16, and a reading unit 17.

Arithmetic unit 11 is an arithmetic main body (an arithmetic device) that performs various processes by executing various programs, and is an example of a computer such as a processor. For example, arithmetic unit 11 (processor) is configured by a microcontroller, a central processing unit (CPU), or a micro-processing unit (MPU). Additionally, the processor includes a function of performing various processes by executing programs, but the function may be partially or entirely implemented by a dedicated hardware circuit such as an application specific integrated circuit (ASIC) or a field-programmable gate array (FPGA). The "processor" is not strictly limited to processors that perform processes by a stored-program method, such as the CPU or the MPU, and may include a hard-wired circuit such as the ASIC or the FPGA. Accordingly, the processor may be read as processing circuitry where a process is defined in advance by a computer-readable code and/or a hard-wired circuit. Additionally, the processor may be configured by one chip, or may be configured by a plurality of chips. Moreover, the processor and related processing circuitry may be configured by a plurality of computers that are interconnected in a wired or wireless manner over a local area network, a wireless network or the like. The processor and related processing circuitry may be configured by a cloud computer that remotely performs computation based on input data and that outputs a computation result to another device at a separate location. Additionally, arithmetic unit 11 may be configured by at least one of a CPU, an FPGA, and a GPU, or a CPU and an FPGA, an FPGA and a GPU, a CPU and a GPU, or all of a CPU, an FPGA, and a GPU. Furthermore, one or some or all of the functions of arithmetic unit 11 may be provided in a server apparatus (such as a cloud server apparatus), not shown.

Storage unit 12 includes a volatile storage area (such as a working area) that temporarily stores a program code, a work memory and the like at the time of execution of an unspecified program by arithmetic unit 11. Storage unit 12 may be one or more non-transitory computer readable media. For example, storage unit 12 is configured by a volatile memory device such as a dynamic random access memory (DRAM) or a static random access memory (SRAM). Furthermore, storage unit 12 includes a non-volatile storage area. Storage unit 12 may be one or more computer readable storage media. For example, storage unit 12 is configured by a non-volatile memory device such as a read only memory (ROM), a hard disk, or a solid state drive (SSD).

Additionally, in the present embodiment, an example is illustrated where a volatile storage area and a non-volatile storage area are included in one storage unit 12, but the volatile storage area and the non-volatile storage area may be included in separate storage units. For example, arithmetic unit 11 may include the volatile storage area, and storage unit 12 may include the non-volatile storage area. Data processing apparatus 1 may include a microcomputer including arithmetic unit 11 and storage unit 12.

Storage unit 12 stores a data processing program 121, and an estimation model 122. Data processing program 121 describes an identification process for causing arithmetic unit 11 to generate two-dimensional data from the three-dimensional data acquired by three-dimensional scanner 2, and to identify an object inside a mouth based on the two-dimensional data and estimation model 122.

Estimation model 122 includes a neural network 1221, and a parameter 1222 that is used by neural network 1221. Estimation model 122 is trained (through machine learning) to estimate a type of each of a plurality of objects inside a mouth based on the two-dimensional data, by using training data including the two-dimensional data including position information of each object and a ground truth label indicating the type of each of the plurality of objects.

More specifically, in a training phase, when the two-dimensional data including the position information of each object inside a mouth is input, estimation model 122 extracts, by neural network 1221, feature of respective objects based on the two-dimensional data and estimates the type of each object based on the features that are extracted. Then, based on the estimated type of each object and the ground truth label indicating the type of each object associated with the two-dimensional data, estimation model 122 optimizes parameter 1222 by updating parameter 1222 so that the two match, in the case where the two do not match, while not updating parameter 1222 in the case where the two match. In this manner, with respect to estimation model 122, machine learning is performed through optimization of parameter 1222 based on the training data including the two-dimensional data as input data and the type of each object as ground truth data. Estimation model 122 may thus estimate each of a plurality of objects inside a mouth based on the two-dimensional data of each of the plurality of objects inside the mouth.

Additionally, estimation model 122 that is optimized through training of estimation model 122 will be specifically referred to also as "trained model". That is, estimation model 122 before training and estimation model 122 after training will be collectively referred to as "estimation model", and estimation model 122 after training will be referred to also as "trained model".

Estimation model 122 includes programs for causing arithmetic unit 11 to perform an estimation process and a training process. In the first embodiment, as programs for performing processes dedicated to images, U-Net, SegNet, ENet, ErfNet, VoxNet, 3D ShapeNets, 3D U-Net, Multi-View CNN, RotationNet, OctNet, PointCNN, FusionNet, PointNet, PointNet++, SSCNet, MarrNet, VoxelNet, PAConv, VGGNet, ResNet, DGCNN, KPConv, FCGF, ModelNet40, ShapeNet, SemanticKITTI, SunRGB-D, Vote-Net, LinkNet, Lambda Network, PREDATOR, 3D Medical Point Transformer, PCT, and the like are used as programs for estimation model 122, but other programs such as a feedforward neural network, a recurrent neural network, a graph neural network, Attention Mechanism, and Transformer may also be used as the programs for estimation model 122.

Scanner interface 13 is an interface for connecting to three-dimensional scanner 2, and performs input/output of data between data processing apparatus 1 and three-dimensional scanner 2. Data processing apparatus 1 and three-dimensional scanner 2 are connected in a wired manner using a cable, or in a wireless manner (WiFi, BlueTooth®, etc.).

Communication unit 14 transmits/receives data from the dental laboratory or the automatic manufacturing apparatus mentioned above by wired communication or wireless communication. For example, data processing apparatus 1 transmits, to the dental laboratory or the automatic manufacturing apparatus via communication unit 14, data for making a dental prosthesis generated based on the three-dimensional data.

Display interface 15 is an interface for connecting display 3, and performs input/output of data between data processing apparatus 1 and display 3.

Peripheral appliance interface 16 is an interface for connecting peripheral appliances such as keyboard 4 and mouse 5, and performs input/output of data between data processing apparatus 1 and the peripheral appliances.

Reading unit 17 reads out various pieces of data stored in a removable disk 20 as a storage medium. The storage medium exemplified by removable disk 20 is a non-transitory and tangible computer readable storage medium, and may be any of examples including a compact disc (CD), a digital versatile disc (DVD), a universal serial bus (USB) memory and the like as long as various pieces of data may be recorded. For example, reading unit 17 may acquire data processing program 121 from removable disk 20.

[Configuration of Three-Dimensional Scanner]

Figure 3:
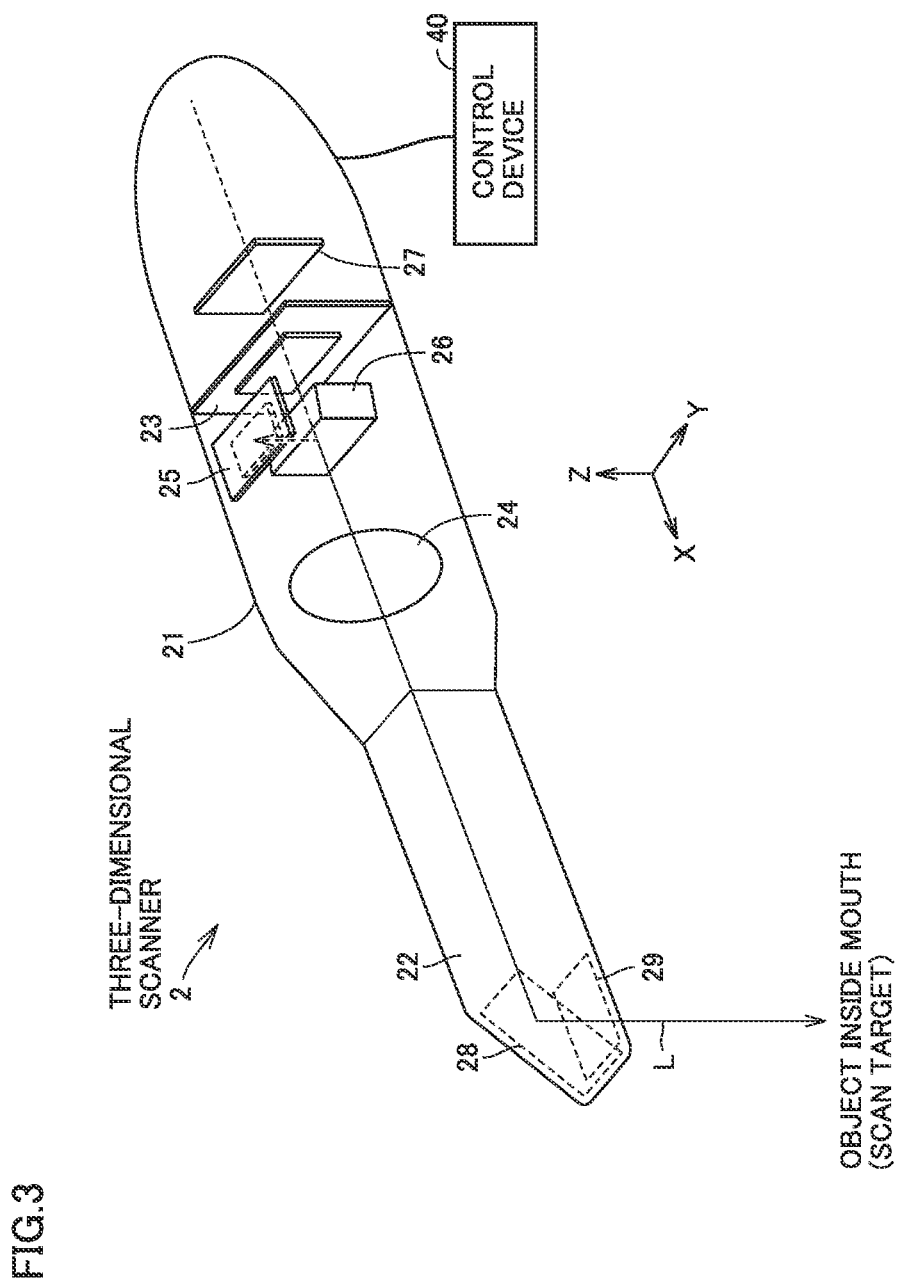
FIG. 3 is a diagram showing a configuration of a three-dimensional scanner according to the first embodiment.
Figure 4:
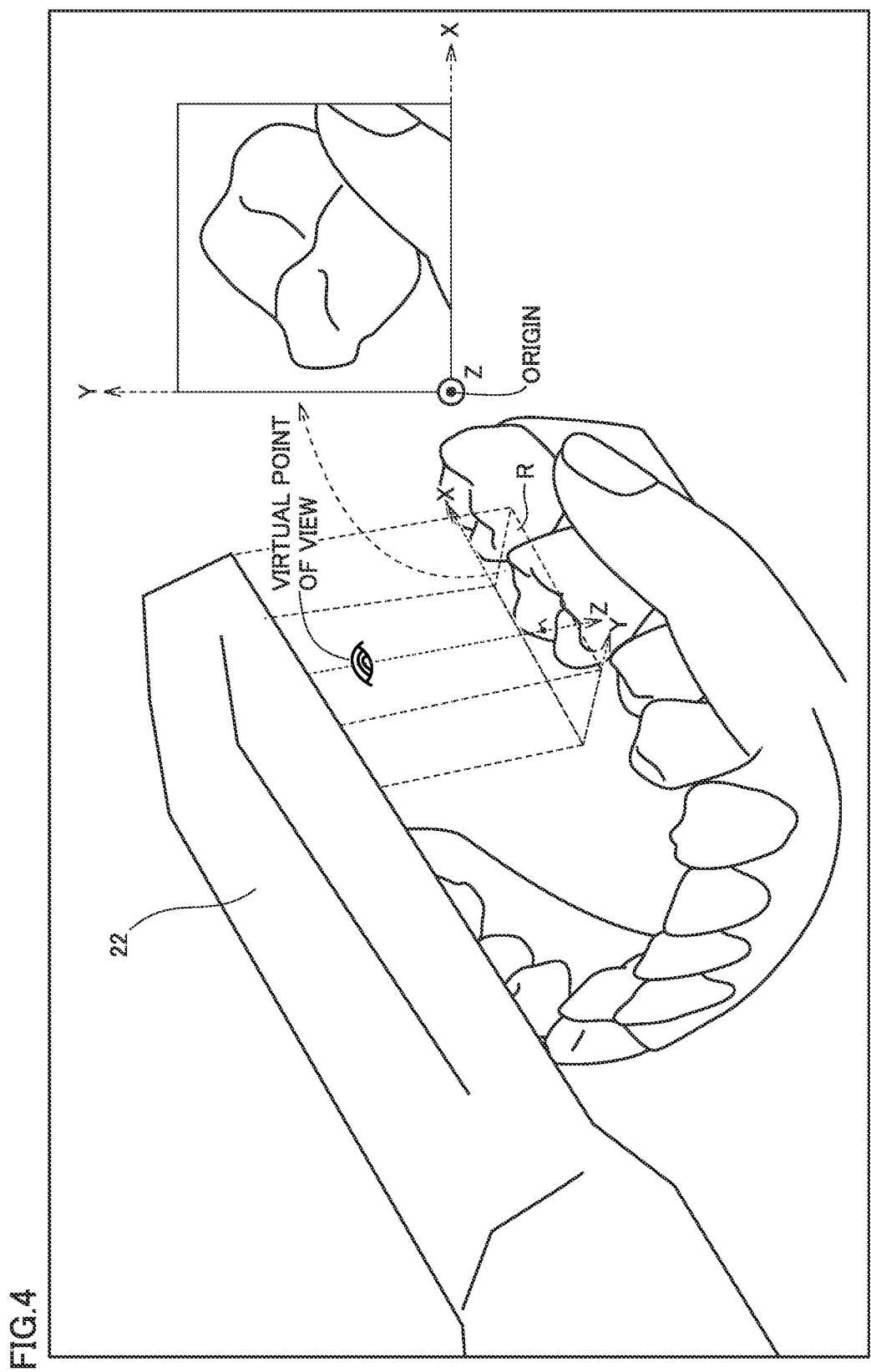
FIG. 4 is a diagram for describing an example of acquisition, based on a confocal method, of three-dimensional data by the three-dimensional scanner according to the first embodiment.

With reference to FIGS. 3 and 4, a configuration of three-dimensional scanner 2 according to the first embodiment will be described. FIG. 3 is a diagram showing a configuration of three-dimensional scanner 2 according to the first embodiment. FIG. 4 is a diagram for describing an example of acquisition, based on a confocal method, of the three-dimensional data by three-dimensional scanner 2 according to the first embodiment.

As shown in FIG. 3, three-dimensional scanner 2 is a hand piece to be held in hand, and includes a housing 21, a probe 22 that is detachably connected to housing 21, and a control device 40.

Probe 22 is inserted into a mouth, and projects light having a pattern (hereinafter also simply referred to as "pattern") onto an object inside the mouth. Probe 22 guides reflected light from an object onto which the pattern is projected, into housing 21.

Three-dimensional scanner 2 includes, inside housing 21, a light source 23, a lens 24, an optical sensor 25, a prism 26, a counterweight 27, and an opening 29. Additionally, in FIGS. 3 and 4, a planar direction parallel to opening 29 will be defined by an X-axis and a Y-axis for the sake of description. Moreover, a direction perpendicular to the X-axis and the Y-axis will be defined by a Z-axis.

Light source 23 includes a laser element, a light emitting diode (LED), or the like. Light (optical axis L) from light source 23 passes through prism 26 and lens 24, is reflected by a reflection unit 28 provided in probe 22, and is output from opening 29. The light that is output from opening 29 is radiated onto an object along a Z-axis direction, and is reflected by the object. That is, an optical axis direction of light that is output from three-dimensional scanner 2 coincides with the Z-axis direction and is perpendicular to the planar direction set by the X-axis and the Y-axis.

The light that is reflected by the object enters housing 21 again through opening 29 and reflection unit 28, passes through lens 24, and is input to prism 26. Prism 26 changes a traveling direction of the light from the object to a direction where optical sensor 25 is positioned. The light, the traveling direction of which is changed by prism 26, is detected by optical sensor 25.

In the case of acquiring the three-dimensional data of an object using a technique according to the confocal method, light having a pattern such as a checkered pattern that passed through a pattern generation element (not shown) provided between lens 24 and the object is projected onto the object in a scan range R. When lens 24 linearly moves to and from along a same straight line, a focal position of the pattern that is projected on the object changes on the Z-axis. Optical sensor 25 detects light from the object every time the focal position changes on the Z-axis.

For example, control device 40 is configured by a CPU, a ROM, a RAM and the like, and controls processes performed by three-dimensional scanner 2. Additionally, control device 40 may be configured by an FPGA or a GPU. Furthermore, control device 40 may be configured by at least one of a CPU, an FPGA, and a GPU, or may be configured by a CPU and an FPGA, an FPGA and a GPU, a CPU and a GPU, or all of a CPU, an FPGA, and a GPU. Moreover, control device 40 may be configured by processing circuitry. Control device 40 calculates position information of each point of a point group indicating a surface of an object, based on a position of lens 24 and a detection result from optical sensor 25 at a corresponding time.

Three-dimensional scanner 2 thereby acquires the position information (an X-coordinate and a Y-coordinate), on an XY plane in scan range R, of each point of a point group indicating the surface of an object. As shown in FIG. 4, in the case where an object is seen along the Z-axis direction from a virtual point of view between three-dimensional scanner 2 and the object, a two-dimensional image showing a surface of the object may be shown on the XY plane. By sequentially acquiring, in the Z-axis direction, a bundle of two-dimensional data including the X-coordinate and the Y-coordinate, three-dimensional scanner 2 may acquire the three-dimensional data (the X-coordinate, the Y-coordinate, and a Z-coordinate) of an object per one scan. One scan corresponds to acquisition of the three-dimensional data (the X-coordinate, the Y-coordinate, and the Z-coordinate) of an object that is performed once in a state where the position of probe 22 of three-dimensional scanner 2 is fixed.

More specifically, in the case where scan is performed once in such a way as to acquire the three-dimensional data along a fixed optical axis in a state where three-dimensional scanner 2 is not moved, control device 40 gives three-dimensional position information to each point of a point group indicating a surface of a scan target object, by taking the optical axis direction as the Z-coordinate and the planar direction perpendicular to the optical axis direction (the Z-axis direction) as the X-coordinate and the Y-coordinate. In the case where scan is performed a plurality of times by three-dimensional scanner 2, when combining, in relation to a plurality of scans, the three-dimensional data of the point group acquired by each scan, control device 40 combines the three-dimensional data based on matching shapes of overlapping parts. Control device 40 re-assigns, at the time of completion of combination or at a certain timing, the X-coordinate, the Y-coordinate, and the Z-coordinate that are based on an unspecified origin, to the combined three-dimensional data of the point group, and thereby acquires the three-dimensional data, unified as a whole, of the point group including the position information of the object.

The three-dimensional data of the object that is acquired by three-dimensional scanner 2 is input to data processing apparatus 1 via scanner interface 13. Additionally, functions of control device 40 may be partially or entirely provided in data processing apparatus 1. For example, arithmetic unit 11 of data processing apparatus 1 may include the functions of control device 40.

[Example of Scanning by Three-Dimensional Scanner]

With reference to FIGS. 5 to 8, an example of scanning by three-dimensional scanner 2 will be described.

Figure 5:
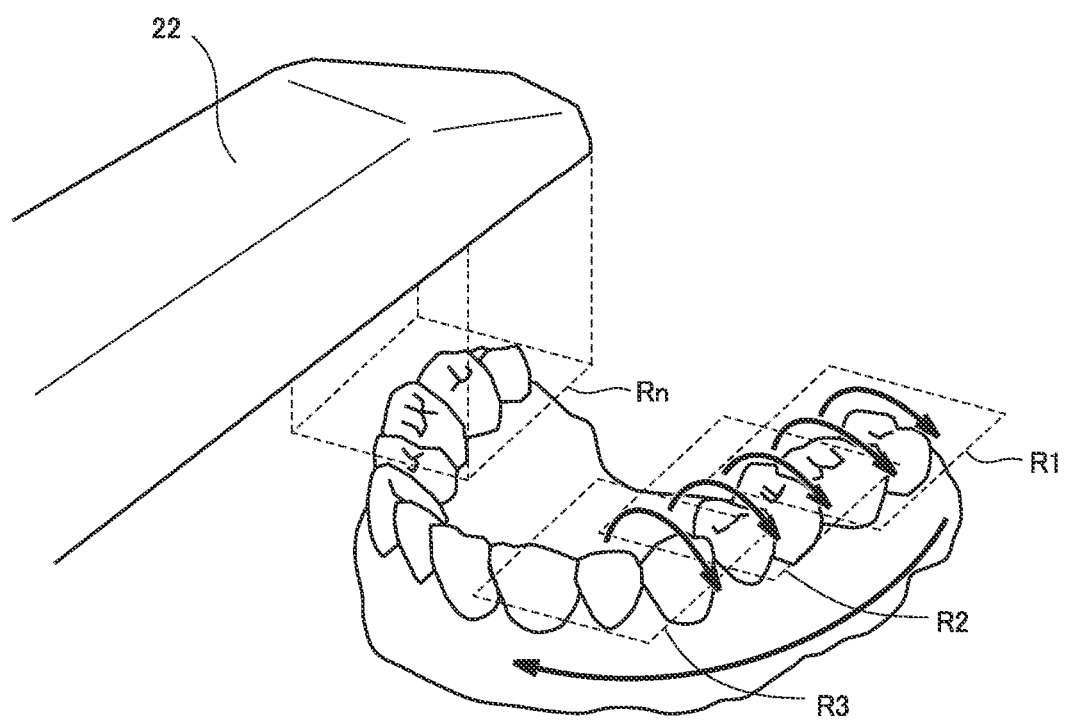
FIG. 5 is a diagram for describing a scan method of the three-dimensional scanner.

FIG. 5 is a diagram for describing a scan method of three-dimensional scanner 2. A scan range of three-dimensional scanner 2 is limited by a size of probe 22 that can be inserted into a mouth. Accordingly, the user inserts probe 22 into a mouth, and scans inside of the mouth a plurality of times by moving probe 22 inside the mouth along a tooth row.

For example, as shown in FIG. 5, the user acquires the three-dimensional data of various parts inside the mouth by sequentially switching the scan range in the manner of R1, R2, R3, . . . , Rn by moving probe 22 inside the mouth. More specifically, the user scans some teeth by moving probe 22 from lingual surfaces of the teeth to labial surfaces of the teeth across occlusal surfaces, and sequentially performs such scanning of a plurality of teeth by moving probe 22 from a left molar side to a right molar side across incisors. Additionally, the manner of moving probe 22 inside a mouth is different for each user or for each dental treatment, and parts inside the mouth where the three-dimensional data is acquired and acquisition order may be changed.

Figure 6:
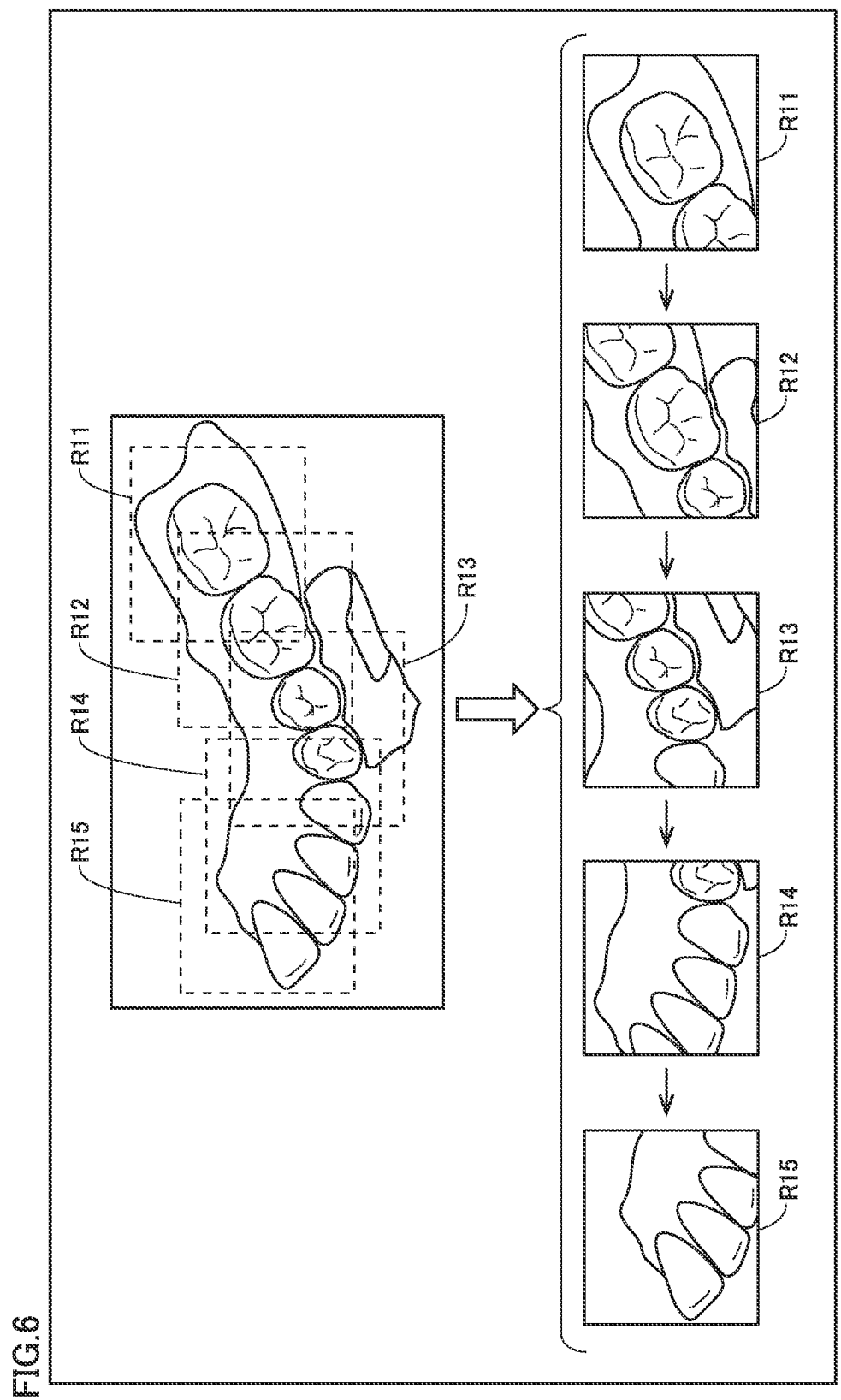
FIG. 6 is a diagram showing an object in each scan range acquired by the three-dimensional scanner according to the first embodiment.

FIG. 6 is a diagram showing an object in each scan range acquired by three-dimensional scanner 2 according to the first embodiment. As shown in FIG. 6, when the user scans objects while moving probe 22, three-dimensional scanner 2 may acquire the three-dimensional data of the object included in each scan range. For example, three-dimensional scanner 2 may acquire the three-dimensional data in one scan range in one scan, and in the example in FIG. 6, three-dimensional scanner 2 may acquire the three-dimensional data in each of scan ranges R11 to R15. Three-dimensional scanner 2 may acquire the three-dimensional data of all the objects included in a plurality of scan ranges R11 to R15 by combining a plurality of pieces of three-dimensional data corresponding, respectively, to the plurality of scan ranges R11 to R15 obtained by a plurality of scans.

Figure 7:
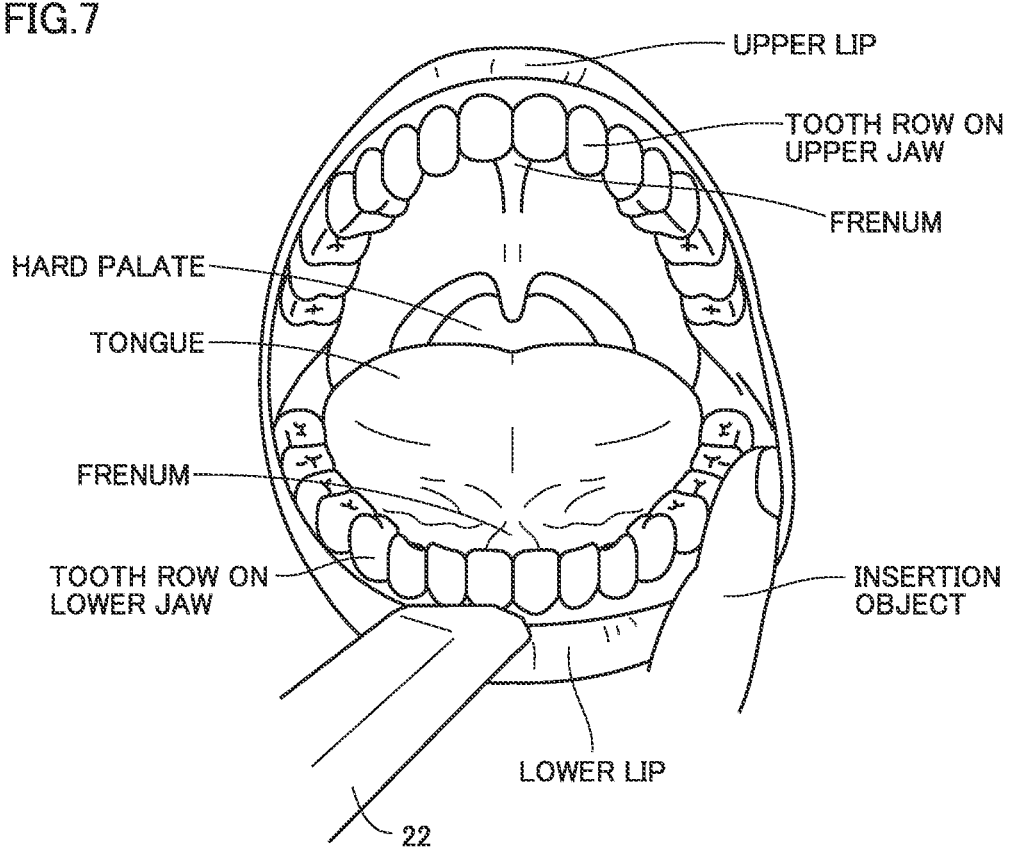
FIG. 7 is a diagram showing a manner of scanning an object using the three-dimensional scanner.
Figure 8:
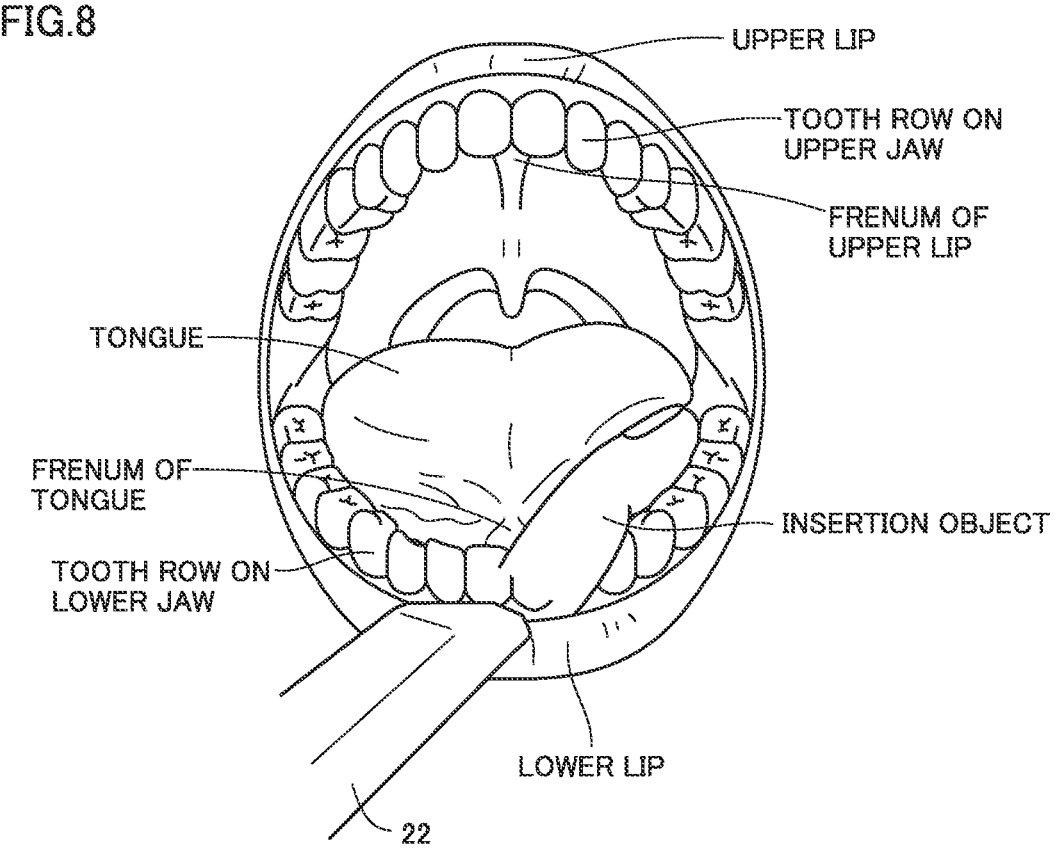
FIG. 8 is a diagram showing a manner of scanning an object using the three-dimensional scanner.

FIGS. 7 and 8 are diagrams each showing a manner of scanning an object using three-dimensional scanner 2. As shown in FIGS. 7 and 8, inside a mouth, there are a plurality of objects such as a tongue, a frenum between a tooth row on a lower jaw and the tongue, the tooth row on the lower jaw, a frenum (not shown) between the tooth row on the lower jaw and a lower lip, the lower lip, a hard palate, a frenum between a tooth row on an upper jaw and the hard palate, the tooth row on the upper jaw, a frenum (not shown) between the tooth row on the upper jaw and an upper lip, the upper lip, gums, mucous membranes, and dental prostheses (metal tooth, ceramic tooth, resin tooth). During scanning by three-dimensional scanner 2, an unnecessary object, such as a finger of a surgeon, a treatment instrument, or a tongue, a lip, or a mucous membrane (an inside lining of a cheek) of a patient, may come between an object as a scan target, such as a tooth, and three-dimensional scanner 2, and three-dimensional scanner 2 may sometimes fail to appropriately acquire the three-dimensional data of the object. For example, in the example in FIG. 6, a finger that is an unnecessary object is captured in ranges R12 to R14. Additionally, a finger is not limited to a bare finger of a surgeon, and a finger of a surgeon wearing a glove is also included.

Furthermore, as the treatment instrument, dental instruments such as a dental vacuum, a mouth gag, a tongue depressor, and the like may be cited.

For example, as shown in FIGS. 7 and 8, at the time of insertion of probe 22 of three-dimensional scanner 2 into a mouth, a finger is sometimes inserted between teeth and a lip to press down soft tissue inside the mouth.

More specifically, as shown in FIG. 7, in the case of acquiring three-dimensional data of a labial surface side of a tooth, the user inserts probe 22 into a gap between the tooth and a lip, and at this time, soft tissue is pressed down by inserting a finger into the gap between the tooth row and the lip to prevent the soft tissue from interfering with scanning. Furthermore, as shown in FIG. 8, in the case of acquiring three-dimensional data of a lingual surface side of a tooth, the user inserts probe 22 into a gap between the tooth row and the tongue, and at this time, soft tissue is pressed down by inserting a finger into the gap between the tooth row and the tongue to prevent the soft tissue from interfering with scanning. Additionally, instead of a finger, a treatment instrument for pressing down the soft tissue may be inserted into the gap between the tooth and the lip or the gap between the tooth and the tongue. When the inside of the mouth is scanned in a state where a finger pressing down the soft tissue is in contact with a tooth row, the three-dimensional data is acquired in a state where the finger that is an unnecessary object is captured in ranges R12 to R14, as shown in FIG. 6.

In this manner, in a dental treatment, the inside of a mouth is usually scanned in a state where an insertion object such as a finger or a treatment instrument is inserted inside the mouth, but three-dimensional scanner 2 sometimes fails to appropriately acquire the three-dimensional data of an object due to the insertion object being captured in the scan range in the manner shown by scan range R in FIG. 4 and scan ranges R12 to R14 in FIG. 6.

Accordingly, data processing apparatus 1 according to the first embodiment uses artificial intelligence (AI), and identifies a type of each of a plurality of objects such as a tooth inside a mouth, a tongue, a lip, a frenum, a gum, a mucous membrane, a dental prosthesis (metal tooth, ceramic tooth, resin tooth), and an insertion object inserted inside the mouth, and extracts and deletes the three-dimensional data of an object that is not necessary for dental treatment based on an identification result. In the following, a specific function of data processing apparatus 1 will be described.

[Functional Configuration of Data Processing Apparatus]

Figure 9:
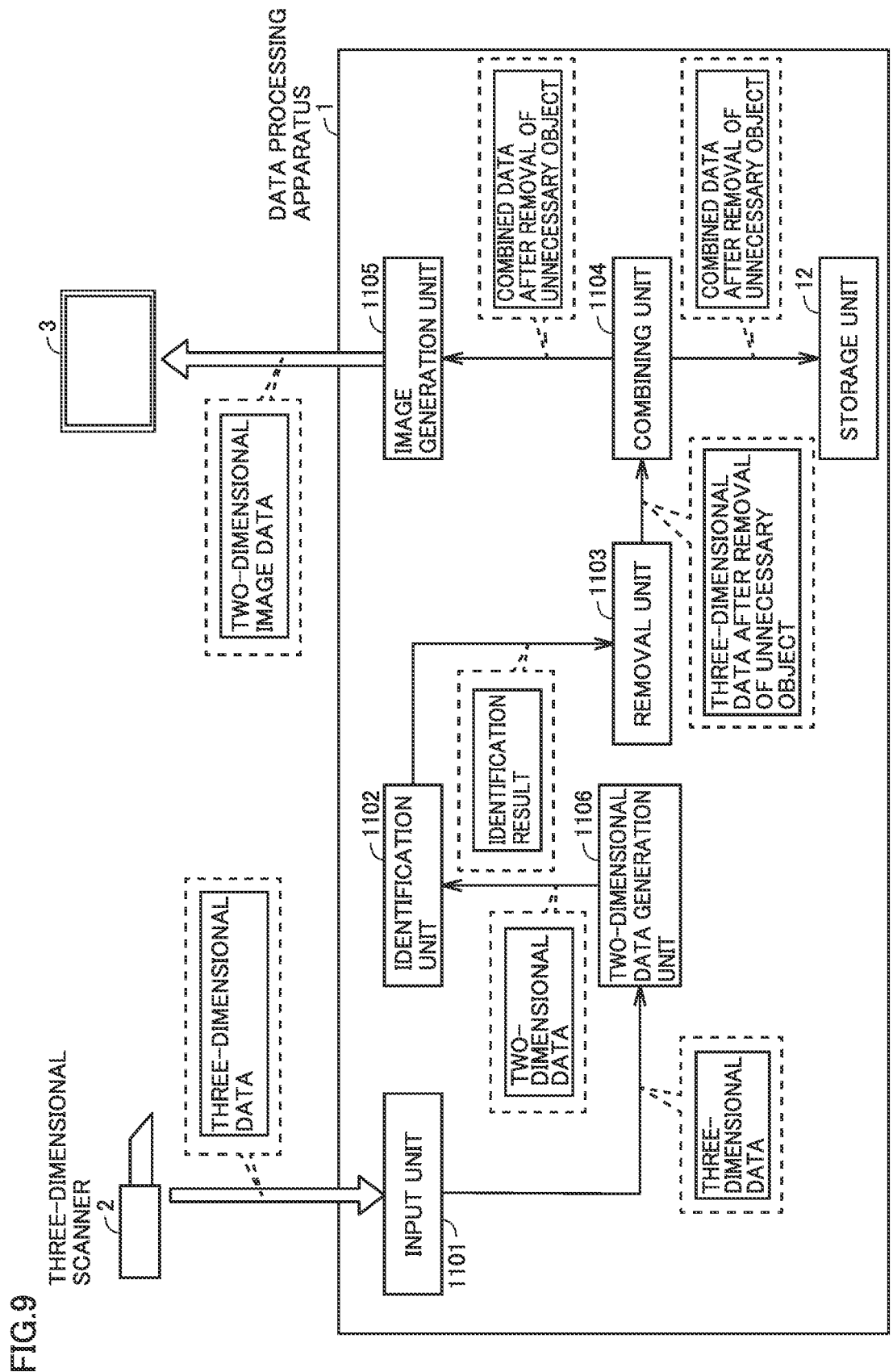
FIG. 9 is a block diagram showing a functional configuration of the data processing apparatus according to the first embodiment.

With reference to FIG. 9, a functional configuration of data processing apparatus 1 according to the first embodiment will be described. FIG. 9 is a block diagram showing the functional configuration of data processing apparatus 1 according to the first embodiment.

As shown in FIG. 9, data processing apparatus 1 includes, as main functional units, an input unit 1101, a two-dimensional data generation unit 1106, an identification unit 1102, a removal unit 1103, a combining unit 1104, an image generation unit 1105, and storage unit 12.

Input unit 1101 is a functional unit of scanner interface 13, and acquires the three-dimensional data of one scan that is acquired by three-dimensional scanner 2. Additionally, input unit 1101 may be a functional unit of communication unit 14, peripheral appliance interface 16, or reading unit 17. For example, in the case where input unit 1101 is a functional unit of communication unit 14, communication unit 14 acquires the three-dimensional data from an external apparatus via wired communication or wireless communication. Additionally, the external apparatus may be a server apparatus installed in a dental clinic, or may be a cloud server apparatus installed at a place different from the dental clinic. In the case where input unit 1101 is a functional unit of peripheral appliance interface 16, peripheral appliance interface 16 acquires the three-dimensional data that is input by the user using keyboard 4 and mouse 5. In the case where input unit 1101 is a functional unit of reading unit 17, reading unit 17 acquires the three-dimensional data that is stored in removable disk 20.

Now, with reference to FIG. 10, the three-dimensional data that is input to data processing apparatus 1 will be described. FIG. 10 is a diagram for describing the three-dimensional data that is input to data processing apparatus 1 according to the first embodiment. As shown in FIG. 10, the three-dimensional data of one scan that is input to input unit 1101 includes position information related to the X-coordinate, the Y-coordinate, and the Z-coordinate, and normal line information related to an X-component, a Y-component, and a Z-component, that are associated with each point of a point group indicating the surface of an object in the scan range. Additionally, although not shown, the three-dimensional data also includes color information that is associated with each point of the point group indicating the surface of an object in the scan range.

As described with reference to FIG. 4, the position information is the X-coordinate, the Y-coordinate, and the Z-coordinate of each point of a point group indicating the surface of an object included in the scan range. The normal line information is the X-component, the Y-component, and the Z-component of a normal line that is, when focusing on one point included in the point group, perpendicular to a tangent line at the focused point. Additionally, a known technique such as principal component analysis may be used for generation of the normal line at one point included in the point group.

Referring to FIG. 9 again, two-dimensional data generation unit 1106 is a functional unit of arithmetic unit 11. Two-dimensional data generation unit 1106 generates two-dimensional data from the three-dimensional data of one scan that is input from input unit 1101.

More specifically, as described with reference to FIG. 4, by detecting light from an object included in a scan range, three-dimensional scanner 2 using the technique of the confocal method is able to acquire the three-dimensional data including the position information of each point of a point group indicating the surface of the object. As shown in FIG. 10, the three-dimensional data that is acquired by three-dimensional scanner 2 and that is input from input unit 1101 includes, as the position information, the X-coordinate, the Y-coordinate, and the Z-coordinate of each point of the point group indicating the surface of the object, and includes color information at a corresponding position. Two-dimensional data generation unit 1106 generates the two-dimensional data of each point of the point group indicating the surface of the object, by using only the X-coordinate and the Y-coordinate in the position information that is included in the three-dimensional data input from input unit 1101. The X-coordinate and the Y-coordinate indicate a pixel position in the two-dimensional data, and the color information is a pixel value at the pixel position. That is, the two-dimensional data that is generated by two-dimensional data generation unit 1106 based on the three-dimensional data is data corresponding to a two-dimensional image showing an external appearance of at least one object included in a scan range, where the at least one object is displayed as seen from a position or point of view that is separate from the at least one object by a certain distance (such as a virtual point-ofview position in FIG. 4). Two-dimensional data generation unit 1106 outputs the two-dimensional data that is generated to identification unit 1102.

Additionally, two-dimensional data generation unit 1106 may generate the two-dimensional data by taking, as a distance image, each point of the point group that indicates the surface of the object by using the X-coordinate, the Y-coordinate, and the Z-coordinate in the position information that is included in the three-dimensional data input from input unit 1101. That is, two-dimensional data generation unit 1106 may take the X-coordinate and the Y-coordinate as a pixel position in the two-dimensional data, and may convert the Z-coordinate into the pixel value at the pixel position. The distance image is two-dimensional data where the Z-coordinate is expressed by color information including a color tone of the image. Moreover, two-dimensional data generation unit 1106 may generate both the two-dimensional data indicating the surface of the object using only the X-coordinate and the Y-coordinate, and the two-dimensional data that uses the distance image that is generated using the X-coordinate, the Y-coordinate, and the Z-coordinate. Using the Z-coordinate as the color information in the manner described above is advantageous in the case where a human visually looks at the two-dimensional image (the distance image). For example, in the distance image (the image in which the Z-coordinate is converted into a pixel value) of a back tooth that is scanned from above, a color that is close to white is obtained around an occlusal surface of the tooth, and a color that is close to black is obtained on a deeper side of the gum. That is, a height difference of the back tooth may be expressed by black and white. In contrast, in the case of a regular two-dimensional image such as a color photograph, the shape of the back tooth is expressed by colors or a contour on the XY plane, and the height difference cannot be expressed. Especially with machine learning, in the case where it is difficult to determine whether a scanned object is a gum, a mucous membrane (an inside lining of a cheek), or a lip based only on the two-dimensional image such as the color photograph, each object may be identified by using the distance image including the height difference as described above. Moreover, in the case where the pixel value is used as the Z-coordinate as in the distance image, a computer (AI) such as arithmetic unit 11 is also enabled to easily perform computation using convolution because a relationship between adjacent objects can be easily grasped compared to when the height of a shape is simply used as the Z-coordinate.

Identification unit 1102 is a functional unit of arithmetic unit 11. Identification unit 1102 identifies at least one object among a plurality of objects, based on the two-dimensional data input from two-dimensional data generation unit 1106 and estimation model 122. Identification unit 1102 outputs the identification result to removal unit 1103.

Now, with reference to FIG. 11, machine learning of estimation model 122 will be described. FIG. 11 is a diagram for describing training data that is used at a time of machine learning of estimation model 122 according to the first embodiment. As shown in FIG. 11, with respect to estimation model 122 according to the first embodiment, machine learning (supervised learning) is performed such that each of a plurality of objects is estimated based on the two-dimensional data of one scan, by using the training data for one scan including the two-dimensional data including the X-coordinate and the Y-coordinate, as the position information of each of a plurality of objects inside a mouth, and the ground truth label indicating each of the plurality of objects. That is, with respect to estimation model 122, machine learning is performed such that an object is estimated based on the two-dimensional data including the X-coordinate and the Y-coordinate, without using the Z-coordinate.

Now, a relative positional relationship between a plurality of objects will be described. Inside a mouth, the position of each of a plurality of objects such as teeth and a tongue are anatomically determined in advance based on a relationship to a certain landmark, or in other words, a relative relationship. For example, as shown in FIGS. 7 and 8 described above, in a state where a face with an open mouth is seen from a front, on the lower jaw, the tongue, the frenum between the tooth row on the lower jaw and the tongue, the tooth row on the lower jaw, the frenum (not shown) between the tooth row on the lower jaw and the lower lip, and the lower lip are positioned in order from around a center of the upper jaw or the lower jaw (on a back side in the mouth) toward an outside (in a direction of opening) In other words, in the case where the tooth row on the lower jaw is taken as a starting point (a certain landmark), the tongue is positioned closer to the back side in the mouth than the tooth row on the lower jaw, and the lower lip is positioned closer to a front side of the mouth than the tooth row on the lower jaw. Furthermore, in a state where the face with the open mouth is seen from the front, on the upper jaw, the hard palate, the frenum between the tooth row on the upper jaw and the hard palate, the tooth row on the upper jaw, the frenum (not shown) between the tooth row on the upper jaw and the upper lip, and the upper lip are positioned in order from around the center of the upper jaw or the lower jaw (on the back side in the mouth) toward the outside (in the direction of opening). In other words, in the case where the tooth row on the upper jaw is taken as a starting point (a certain landmark), the hard palate is positioned closer to the back side in the mouth than the tooth row on the upper jaw, and the upper lip is positioned more in the direction of opening of the mouth than the tooth row on the upper jaw. That is, a relative positional relationship among a plurality of objects such as teeth, tongue, and lips is fixed inside a mouth.

In this manner, the relative positional relationship of a plurality of objects inside a mouth is fixed, and thus, it can be said that there is a correlation between the three-dimensional data including the position information of an object as input data of estimation model 122, and the identification result of the type of the object as output data of estimation model 122. That is, there is a correlation between the input data and the output data as exemplified by association between the position information of an object included in the three-dimensional data and the type of the object, and thus, estimation model 122 may, based on the three-dimensional data including the position information of an object that is input, identify the type of the object by specifying a region inside the mouth where the position corresponding to the three-dimensional data is included.

FIG. 12 is a diagram for describing a correspondence relationship between each of a plurality of objects and the ground truth label. As shown in FIG. 12, on the lower jaw, with respect to the tongue, data indicating "01" is associated as the ground truth label. With respect to the lower jaw first gap, data indicating "02" is associated as the ground truth label. With respect to each of a plurality of teeth included in the tooth row on the lower jaw, data indicating "31", . . . , "48" is associated as the ground truth label. With respect to the lower jaw second gap, data indicating "04" is associated as the ground truth label. With respect to the lower lip, data indicating "05" is associated as the ground truth label.

With respect to the upper jaw, data indicating "06" is associated, as the ground truth label, with the hard palate.

Data indicating "07" is associated, as the ground truth label, with the upper jaw first gap. Data indicating "11", ..., "28" is associated, as the ground truth label, with each of a plurality of teeth included in the tooth row on the upper jaw. Data indicating "09" is associated, as the ground truth label, with the upper jaw second gap. Data indicating "10" is associated, as the ground truth label, with the upper lip.

As described above, in a dental treatment, an insertion object such as a finger or a treatment instrument may be inserted into the mouth. Among the insertion objects, data indicating "51" is associated, as the ground truth label, with a finger. Moreover, among the insertion objects, data indicating "52" is associated, as the ground truth label, with a treatment instrument.

Referring to FIG. 11 again, in the training data, the ground truth label indicating the type of an object is associated with the two-dimensional data (the position information) of each point of the point group indicating the surface of each of a plurality of objects obtained by one scan.

For example, as shown in FIG. 11, the data indicating "01" is associated, as the ground truth label, with the two-dimensional data that is generated from the three-dimensional data that is obtained by scanning the tongue. The data indicating "38" is associated, as the ground truth label, with the two-dimensional data that is generated from the three-dimensional data that is obtained by scanning a left third molar on the lower jaw. The data indicating "37" is associated, as the ground truth label, with the two-dimensional data that is generated from the three-dimensional data that is obtained by scanning a left second molar on the lower jaw. Moreover, the data indicating "51" is associated, as the ground truth label, with the two-dimensional data that is generated from the three-dimensional data that is obtained by scanning a finger inserted in the lower jaw second gap.

In this manner, in the first embodiment, as the training data for machine learning of estimation model 122, the ground truth label indicating the type of an object is associated with the two-dimensional data (the X-coordinate, the Y-coordinate) of each point of the point group indicating the surface of each of a plurality of objects obtained by one scan.

Based on the two-dimensional data of one scan, estimation model 122 identifies the type of each of a plurality of objects that are scanned, and adjusts parameter 1222 based on a degree of match between the identification result and the ground truth label.

Estimation model 122 is thus able to identify the type of an object corresponding to the two-dimensional data by performing machine learning to identify the type of an object corresponding to the two-dimensional data based on the ground truth label associated with the two-dimensional data of one scan.

Moreover, because estimation model 122 performs machine learning based on the two-dimensional data that is dimensionally reduced with regard to the Z-coordinate, machine learning may be performed while reducing the burden of computation processing compared to a case where the three-dimensional data including the Z-coordinate is used.

Referring to FIG. 9 again, removal unit 1103 is a functional unit of arithmetic unit 11. Removal unit 1103 acquires the identification result indicating the type of an object from identification unit 1102. As shown in FIG. 12, identification results include identification results for insertion objects such as a finger and a treatment instrument as well as the identification result for each of the tongue, the lower jaw first gap, each tooth of the tooth row on the lower jaw, the lower jaw second gap, the lower lip, the hard palate, the upper jaw first gap, each tooth of the tooth row on the upper jaw, the upper jaw second gap, and the upper lip. In the case where an identification result indicating an unnecessary object such as the finger of the surgeon, the treatment instrument, or the tongue of the patient is included in the identification results from identification unit 1102, removal unit 1103 generates the three-dimensional data after removal of the unnecessary object by removing, from the three-dimensional data input from input unit 1101, three-dimensional data (hereinafter referred to also as "unnecessary three-dimensional data") including the position information of each point of a point group indicating the surface of the unnecessary object identified by identification unit 1102.

More specifically, removal unit 1103 extracts the unnecessary three-dimensional data by extracting the position information in an XY plane direction (the X-coordinate, the Y-coordinate) of each point of the point group indicating the surface of the unnecessary object and by extracting the position information in the optical axis direction (the Z-coordinate) corresponding to each point of the point group indicating the surface of the unnecessary object. For example, removal unit 1103 extracts the X-coordinate and the Y-coordinate of each point of the point group indicating the surface of the unnecessary object identified by identification unit 1102, based on the two-dimensional data generated by two-dimensional data generation unit 1106.

Furthermore, removal unit 1103 extracts the Z-coordinate that is associated with the X-coordinate and the Y-coordinate of the unnecessary object, based on the three-dimensional data acquired by input unit 1101 and with the X-coordinate and the Y-coordinate of the unnecessary object that are extracted as search keys. Removal unit 1103 may take the X-coordinate, the Y-coordinate, and the Z-coordinate of the unnecessary object that are extracted, as the unnecessary three-dimensional data. Extraction of an unnecessary object here includes storing of identification data that enables identification of the unnecessary object, in association with data of each of the X-coordinate, the Y-coordinate, and the Z-coordinate, for example. Removal unit 1103 may generate the three-dimensional data after removal of the unnecessary object by removing the unnecessary three-dimensional data from the three-dimensional data input from input unit 1101. Removal unit 1103 outputs the three-dimensional data after removal of the unnecessary object to combining unit 1104.

Combining unit 1104 is a functional unit of arithmetic unit 11. Combining unit 1104 acquires the three-dimensional data of one scan from removal unit 1103 every time the three-dimensional data of one scan is input to input unit 1101, combines accumulated pieces of three-dimensional data of a plurality of scans, and generates combined three-dimensional data of the plurality of scans (hereinafter referred to also as "combined data").

FIG. 13 is a diagram for describing the combined data after removal of an unnecessary object, generated by data processing apparatus 1 according to the first embodiment. As shown in FIG. 13, in the case where the identification results from identification unit 1102 include the identification result for an unnecessary object such as the finger of the surgeon, the treatment instrument, or the tongue, the lip, the mucous membrane or the like of the patient, removal unit 1103 sets a remove flag to the three-dimensional data corresponding to the unnecessary object (the unnecessary three-dimensional data) identified by identification unit 1102. In the example in FIG. 13, the remove flag is set to "01" in relation to the unnecessary three-dimensional data corresponding to the tongue, the lip, the mucous membrane, and the finger that are removal targets. Data processing apparatus 1 does not use the unnecessary three-dimensional data where the remove flag is set to "01", in a two-dimensional image to be displayed on display 3. As shown in FIG. 13, based on the three-dimensional data input from removal unit 1103, combining unit 1104 generates the combined data after removal of the unnecessary object, by combining the three-dimensional data of a plurality of scans.

Referring to FIG. 9 again, combining unit 1104 outputs the combined data to storage unit 12 and image generation unit 1105. Storage unit 12 stores the combined data input from combining unit 1104. Image generation unit 1105 is a functional unit of arithmetic unit 11. Image generation unit 1105 generates two-dimensional image data corresponding to a two-dimensional image as seen from an unspecified point of view, based on the combined data input from combining unit 1104, and outputs the two-dimensional image data that is generated to display 3. At this time, image generation unit 1105 generates the two-dimensional image data without using the unnecessary three-dimensional data where the remove flag is set to "01". Data processing apparatus 1 may thus cause the two-dimensional image of inside of the mouth from which the unnecessary object is removed to be displayed on display 3 to be seen by the user.

[Processing Flow of Data Processing Apparatus]

Figure 14:
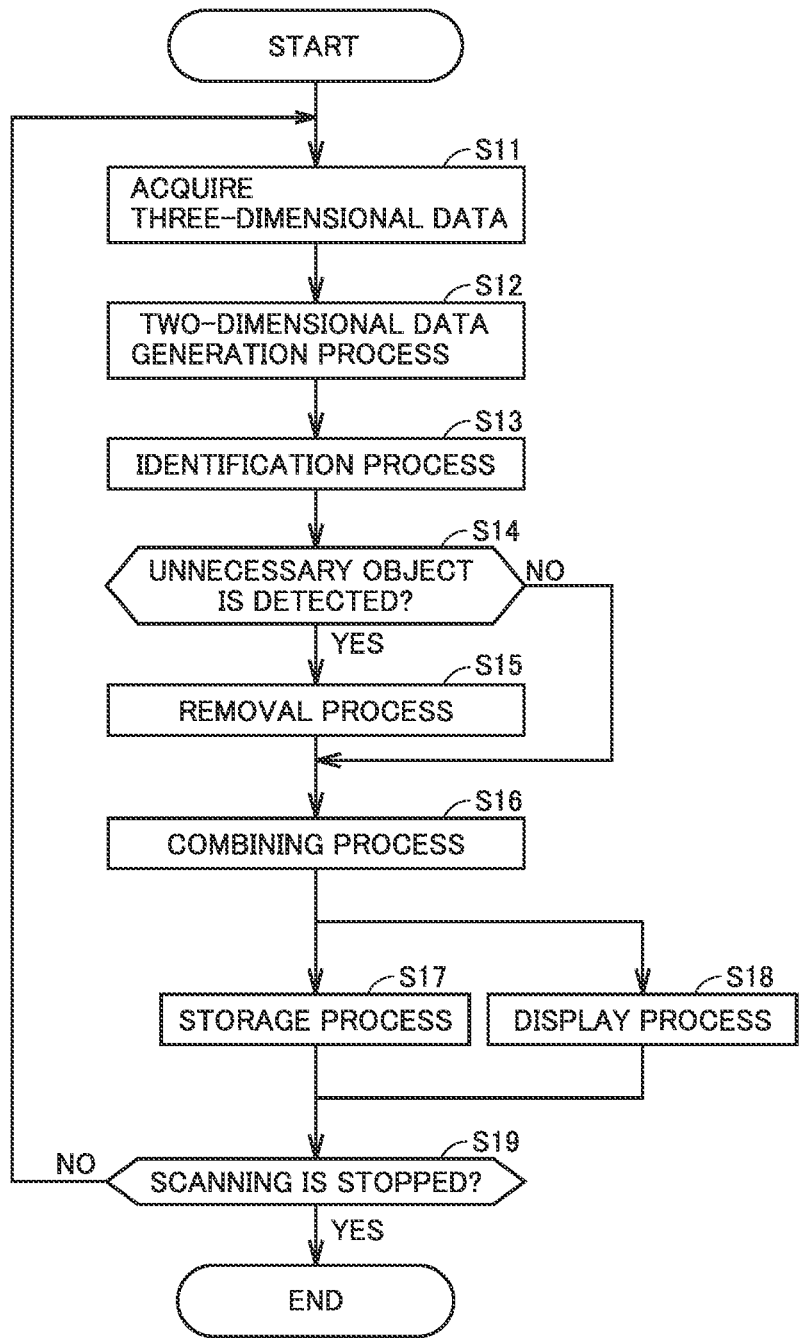
FIG. 14 is a flowchart for describing an example of a process that is performed by the data processing apparatus according to the first embodiment.

With reference to FIG. 14, an example of a process that is performed by data processing apparatus 1 will be described. FIG. 14 is a flowchart for describing an example of the process that is performed by data processing apparatus 1 according to the first embodiment. Each step (hereinafter indicated by "S") shown in FIG. 14 is performed by arithmetic unit 11 of data processing apparatus 1 executing data processing program 121. Furthermore, data processing apparatus 1 performs the process of the flowchart shown in FIG. 14 after scanning by three-dimensional scanner 2 is started.

As shown in FIG. 14, data processing apparatus 1 acquires the three-dimensional data of an unspecified point that is scanned by three-dimensional scanner 2 (S11). Data processing apparatus 1 generates the two-dimensional data from the three-dimensional data that is acquired, using only the X-coordinate and the Y-coordinate (S12). Data processing apparatus 1 identifies each of a plurality of objects that are scanned, based on the two-dimensional data and estimation model 122 (S13).

Data processing apparatus 1 determines whether an unnecessary object is detected or not, based on identification results (S14). That is, data processing apparatus 1 determines whether the data indicating "01" corresponding to the tongue, the data indicating "51" corresponding to a finger, the data indicating "52" corresponding to a treatment instrument, the data indicating "05" corresponding to the lower lip, and the data indicating "10" corresponding to the upper lip are output as the identification results or not. In the case where an unnecessary object is detected (YES in S14), data processing apparatus 1 extracts the unnecessary three-dimensional data corresponding to the unnecessary object that is detected, and removes the unnecessary three-dimensional data that is extracted (S15). That is, data processing apparatus 1 sets the remove flag for the unnecessary three-dimensional data.

In the case where an unnecessary object is not detected (NO in S14), or after the unnecessary three-dimensional data is removed in S15, data processing apparatus 1 generates the combined data by combining the three-dimensional data of a plurality of scans (S16).

Data processing apparatus 1 stores the combined data in storage unit 12 (S17). Moreover, data processing apparatus 1 generates the two-dimensional image data corresponding to the two-dimensional image as seen from an unspecified point of view based on the combined data, outputs the two-dimensional image data that is generated to display 3, and thus causes a two-dimensional image of inside of the mouth to be displayed on display 3 (S18).

Data processing apparatus 1 determines whether scanning by three-dimensional scanner 2 is stopped or not (S19). In the case where scanning by three-dimensional scanner 2 is not stopped (NO in S19), data processing apparatus 1 returns to the process in S11. In the case where scanning by three-dimensional scanner 2 is stopped (YES in S19), data processing apparatus 1 ends the present process.

As described above, data processing apparatus 1 is capable of also identifying, using estimation model 122, an unnecessary object that is not necessary for a dental treatment, among a plurality of objects scanned by three-dimensional scanner 2, and of extracting the unnecessary three-dimensional data including the position information of each point of the point group indicating the surface of the unnecessary object that is identified. Accordingly, the user himself/herself does not have to extract the three-dimensional data of an unnecessary object, and the three-dimensional data of an unnecessary object may be easily and appropriately extracted.

Moreover, because data processing apparatus 1 is capable of identifying each of a plurality of objects inside a mouth by using estimation model 122 and based on the two-dimensional data that is dimensionally reduced with regard to the Z-coordinate, the three-dimensional data of an unnecessary object may be extracted while reducing the burden of computation processing compared to a case where each of a plurality of objects inside a mouth is identified using the three-dimensional data including the Z-coordinate.

Because data processing apparatus 1 is capable of removing the unnecessary three-dimensional data from the three-dimensional data input from three-dimensional scanner 2, the user himself/herself does not have to remove the three-dimensional data of an unnecessary object to generate the three-dimensional data after removal of an unnecessary object, and the three-dimensional data after removal of an unnecessary object may be easily acquired.

Because data processing apparatus 1 outputs, to display 3, image data that is generated using the three-dimensional data after removal of the unnecessary three-dimensional data, the user himself/herself does not have to generate the two-dimensional image of inside of a mouth from which an unnecessary object is removed, and a two-dimensional image after removal of an unnecessary object may be easily acquired.

Second Embodiment

A second embodiment of the present disclosure will be described in detail with reference to the drawings. Additionally, in the second embodiment, only parts that are different from those in the first embodiment will be described, and parts that are the same as those in the first embodiment will be denoted by same reference signs and redundant description will be omitted.

Figure 15:
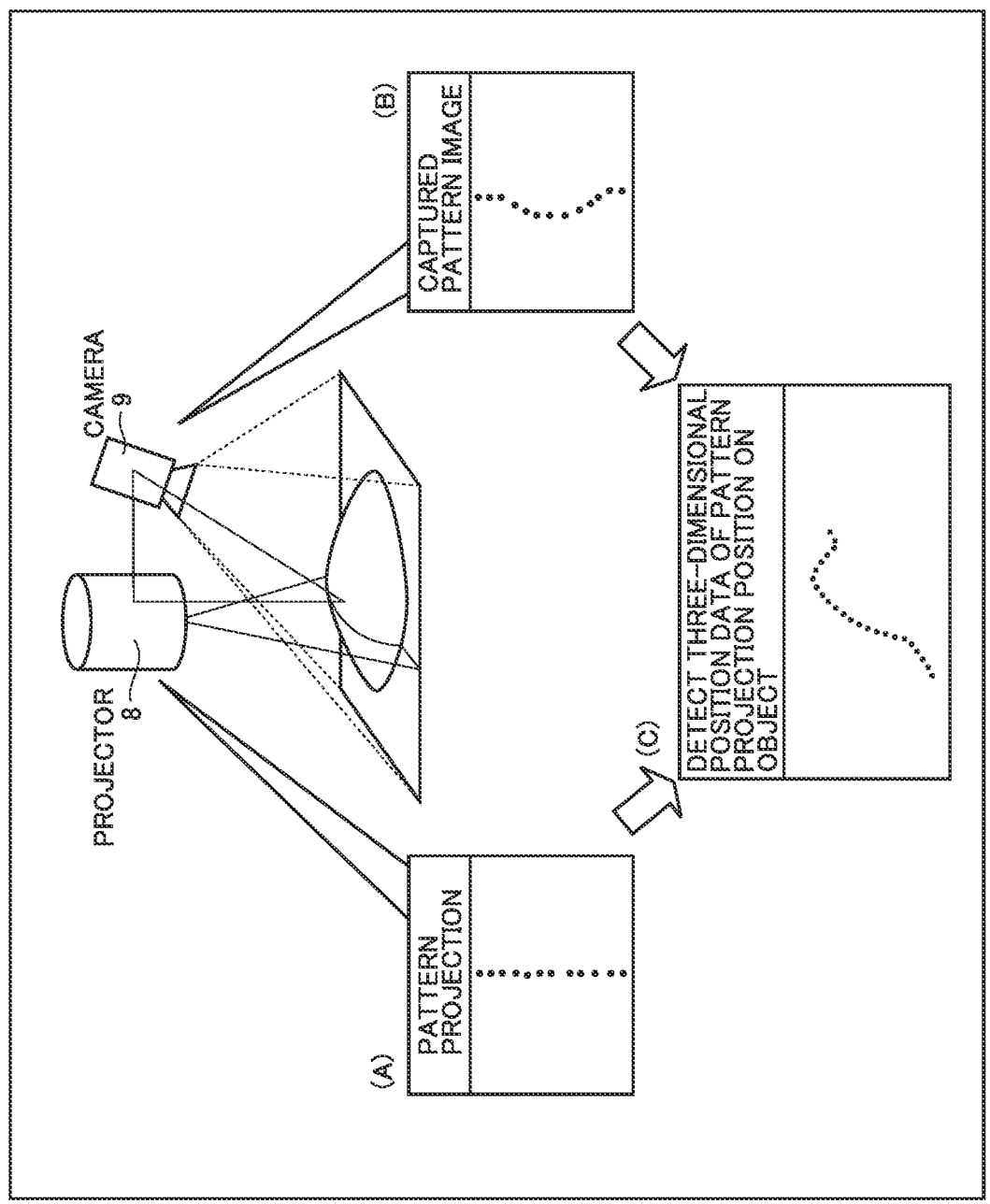
FIG. 15 is a diagram for describing an example of acquisition, based on a triangulation method, of three-dimensional data by a three-dimensional scanner according to a second embodiment.
Figure 16:
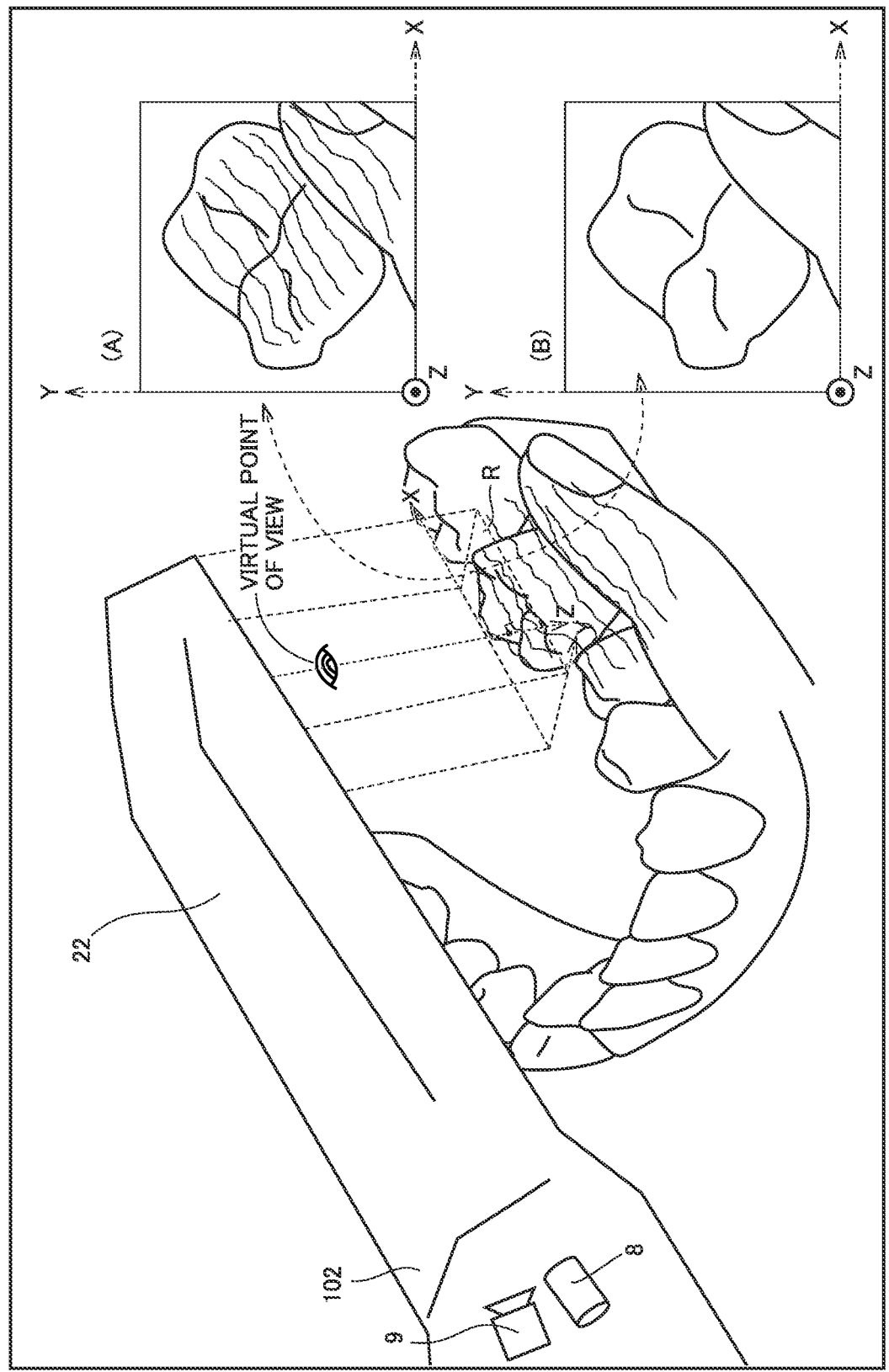
FIG. 16 is a diagram showing a two-dimensional image as seen from an unspecified point of view, based on the three-dimensional data that is acquired by the three-dimensional scanner according to the second embodiment.

FIG. 15 is a diagram for describing an example of acquisition, based on a triangulation method, of three-dimensional data by a three-dimensional scanner 102 according to the second embodiment. FIG. 16 is a diagram showing a two-dimensional image as seen from an unspecified point of view, based on three-dimensional data that is acquired by three-dimensional scanner 102 according to the second embodiment. Unlike three-dimensional scanner 2 according to the first embodiment, three-dimensional scanner 102 according to the second embodiment acquires the three-dimensional data based on the triangulation method.

As shown in FIG. 15, according to the triangulation method, a pattern is projected on an object by a projector 8, and the pattern projected on the object is captured by a camera 9 that is at a position different from projector 8. In the case where projector 8 projects a linear pattern on the object in the manner shown in the pattern projection (A) in FIG. 15(A), a pattern that is along a shape of the object is shown in a pattern image that is obtained by capturing by camera 9 in the manner shown in the captured pattern image (B) in FIG. 15(B), based on an angle formed by a line connecting projector 8 and the object and a line connecting camera 9 and the object. As shown in the position of the pattern (C) in FIG. 15(C), three-dimensional scanner 102 detects a position of the pattern that is projected on the object by using a known triangulation method, based on a length of the line connecting projector 8 and the object, a length of the line connecting camera 9 and the object, a length of a line connecting projector 8 and camera 9, and an angle of each apex of a triangle created by these lines.

As shown in FIG. 16, three-dimensional scanner 102 includes projector 8 that projects a pattern on an object inside a mouth, and camera 9 that captures the pattern that is projected on the object. As shown in a captured image (A) in FIG. 16(A), three-dimensional scanner 102 captures the object by camera 9 in a state where the pattern is projected on the object by projector 8. Three-dimensional scanner 102 acquires, based on a captured image (A) in FIG. 16 (A), the position information (the X-coordinate, the Y-coordinate, the Z-coordinate) of each point of a point group indicating the surface of the object by using a known triangulation method.

Moreover, as shown in a captured image (B) in FIG. 16(B), three-dimensional scanner 102 may also capture the object by camera 9 in a state where the pattern is not projected on the object by projector 8. As described above, data processing apparatus 1 according to the third embodiment identifies each of a plurality of objects inside a mouth based on the two-dimensional data, and data processing apparatus 1 may identify each of a plurality of objects inside a mouth based on a captured image (B) in FIG. 16(B) acquired by three-dimensional scanner 102. Furthermore, by using as search keys the X-coordinate and the Y-coordinate of an unnecessary object that is extracted, data processing apparatus 1 may extract the Z-coordinate of the unnecessary object acquired based on the captured image (A) in FIG. 16(A).

Additionally, three-dimensional scanner 102 may acquire the captured image (A) in FIG. 16(A) and the captured image (B) in FIG. 16(B) by switching between a process of capturing an object by camera 9 in a state where a pattern is projected on the object by projector 8, and a process of capturing the object by camera 9 in a state where the pattern is not projected on the object by projector 8. In one embodiment, three-dimensional scanner 102 may include a plurality of cameras 9, and may acquire the captured image (A) in FIG. 16 (A) and the captured image (B) in FIG. 16(B) by capturing an object by a first camera in a state where a pattern is projected on the object by projector 8, and capturing the object by a second camera in a state where the pattern is not projected on the object by projector 8.

MODIFICATIONS

The present disclosure is not limited to the examples described above, and various modifications and applications are possible. In the following, modifications that are applicable to the present disclosure will be described.

In the embodiments described above, an unnecessary object that is not necessary for a dental treatment is described as "predetermined object", but "predetermined object" is not limited to the unnecessary object and may instead be a specific object that is freely specified in advance by the user. For example, in the case where caries is found in a specific tooth (such as a left third molar on the lower jaw) among a plurality of teeth inside a mouth, the user may pick up only the specific tooth and specify the same as "predetermined object". In this case, data processing apparatus 1 generates the two-dimensional data from the three-dimensional data of inside of the mouth acquired by three-dimensional scanner 2, identifies the specific tooth specified by the user, based on the two-dimensional data that is generated, and extracts predetermined three-dimensional data including the position information of each point of a point group indicating a surface of the specific tooth that is identified.

Identification unit 1102 may identify each of a plurality of objects inside a mouth by pattern matching based on a feature that is designed in advance, or in other words, a preset shape that is included in a two-dimensional image, without being limited to identifying each of a plurality of objects inside a mouth using estimation model 122. As described above, the two-dimensional data that is generated by two-dimensional data generation unit 1106 is data corresponding to a two-dimensional image showing an external appearance of at least one object inside the mouth where the at least one object is displayed as seen from a position or point of view that is separate from the at least one object by a certain distance (such as the virtual point-of-view position in FIG. 4). Identification unit 1102 may recognize a figure or feature of an object (for example, a tooth or an unnecessary object) from a two-dimensional image that is generated by two-dimensional data generation unit 1106 and that shows an external appearance of an object (for example, a tooth or an unnecessary object) that is an identification target inside the mouth, determine a degree of match between the figure of the object (for example, a tooth or an unnecessary object) that is recognized and the feature that is designed in advance, or in other words, the preset shape included in the two-dimensional image, and identify the object (for example, a tooth or an unnecessary object) that is the identification target based on the determination result.

The three-dimensional data that is input to input unit 1101 may include color information (an RGB value) indicating an actual color of each point of a point group indicating the surface of an object, in addition to the position information and the normal line information at each point of the point group. Furthermore, with respect to estimation model 122, machine learning may be performed such that the type of an object is identified based on the color information (the RGB value) that is associated with the three-dimensional data that is input to input unit 1101. Additionally, the three-dimensional data that is input to input unit 1101 may also include only the position information of each point of the point group, without including the normal line information and the color information.

Removal unit 1103 is not limited to removing the unnecessary three-dimensional data, and may also add the color information indicating an unnecessary object to the unnecessary three-dimensional data. Moreover, image generation unit 1105 is not limited to generating the two-dimensional image of inside of the mouth after removal of the unnecessary object, and may also generate a two-dimensional image in which a color indicating an unnecessary object is added to a part corresponding to the unnecessary object, and output the two-dimensional image to display 3.

As three-dimensional measurement methods, triangulation methods such as structure from motion (SfM) and simultaneous localization and mapping (SLAM) that do not use random pattern projection or pattern projection, or a laser technique such as time of flight (TOF) or light detection and ranging (LIDAR) may be used, in addition to the techniques described above.

The embodiments disclosed herein should be considered illustrative and not restrictive in every aspect. The scope of the present disclosure is indicated by the claims and not by the description given above, and is intended to include all the changes within the scope and meaning equivalent to the claims. Additionally, configurations illustrated in the present embodiments and configurations illustrated in the modifications may be combined as appropriate.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A data processing apparatus for processing data including position information of at least one object inside a mouth, the data processing apparatus comprising:
    an input interface to which three-dimensional data including position information of each point of a point group indicating a surface of the at least one object is input; and
    processing circuitry configured to process the three-dimensional data that is input from the input interface, wherein the processing circuitry is further configured to:
        generate two-dimensional data along a planar direction from the three-dimensional data,
        identify a predetermined object among the at least one object, based on the two-dimensional data, and
        extract predetermined three-dimensional data of the predetermined object by extracting position information along the planar direction and a direction perpendicular to the planar direction for each point of the point group indicating the surface of the predetermined object.

2. The data processing apparatus according to claim 1, wherein the predetermined object includes at least one of: an insertion object that is inserted inside the mouth, a tongue, a lip, and a mucous membrane.

3. The data processing apparatus according to claim 2, wherein the insertion object includes at least one of: a finger and a treatment instrument, either of which is inserted to press down soft tissue inside the mouth at a time when an image capturing apparatus for capturing data inside of the mouth is inserted inside the mouth.

4. The data processing apparatus according to claim 1, wherein
    the three-dimensional data that is input from the input interface is acquired by an image capturing apparatus that captures data inside of the mouth based on a confocal method or a triangulation method by being inserted inside the mouth, and
    the direction perpendicular to the planar direction is an optical axis direction of the image capturing apparatus.

5. The data processing apparatus according to claim 4, wherein the processing circuitry is further configured to remove the predetermined three-dimensional data from the three-dimensional data that is input from the input interface.

6. The data processing apparatus according to claim 5, wherein the processing circuitry is further configured to output image data that is generated using the three-dimensional data after removal of the predetermined three-dimensional data.

7. The data processing apparatus according to claim 4, wherein the processing circuitry is configured to add color information indicating the predetermined object to the predetermined three-dimensional data.

8. The data processing apparatus according to claim 1, wherein
    the two-dimensional data that is generated based on the three-dimensional data is data corresponding to a two-dimensional image showing an external appearance of the at least one object where the at least one object is displayed as from a position that is separate from the at least one object by a certain distance, and
    the processing circuitry is configured to identify the predetermined object by recognizing a figure of the predetermined object included in the two-dimensional image.

9. The data processing apparatus according to claim 8, wherein the processing circuitry is configured to extract the predetermined three-dimensional data by extracting position information along the direction perpendicular to the planar direction in the two-dimensional image corresponding to the position information of the predetermined object included in the two-dimensional image.

10. The data processing apparatus according to claim 1, wherein the processing circuitry is configured to identify the predetermined object based on the two-dimensional data and an estimation model that is trained to estimate a type of the predetermined object among the at least one object based on the two-dimensional data.

11. A data processing method of processing data including position information of at least one object inside a mouth, the data processing method comprising:
    receiving, via a computer, three-dimensional data including position information of each point of a point group indicating a surface of the at least one object;
    generating, via the computer, two-dimensional data along a planar direction from the three-dimensional data;
    identifying, via the computer, a predetermined object among the at least one object, based on the two-dimensional data; and
    extracting, via the computer, predetermined three-dimensional data of the predetermined object by extracting position information, along the planar direction and a direction perpendicular to the planar direction, of each point of the point group indicating the surface of the predetermined object.

12. The data processing method according to claim 11, wherein the predetermined object includes at least one of: an insertion object that is inserted inside the mouth, a tongue, a lip, and a mucous membrane.

13. The data processing method according to claim 12, wherein the insertion object includes at least one of: a finger and a treatment instrument, either of which is inserted to press down soft tissue inside the mouth at a time when an image capturing apparatus for capturing data inside of the mouth is inserted inside the mouth.

14. The data processing method according to claim 11, wherein
    the three-dimensional data that is received input from the input interface is acquired by an image capturing apparatus that captures data inside of the mouth based on a confocal method or a triangulation method by being inserted inside the mouth, and the direction perpendicular to the planar direction is an optical axis direction of the image capturing apparatus.

15. The data processing method according to claim 14, further comprising removing the predetermined three-dimensional data from the three-dimensional data that is received.

16. The data processing method according to claim 15, further comprising outputting image data that is generated using the three-dimensional data after removal of the predetermined three-dimensional data.

17. The data processing method according to claim 14, further comprising adding color information indicating the predetermined object to the predetermined three-dimensional data.

18. The data processing method according to claim 11, wherein the two-dimensional data that is generated based on the three-dimensional data is data corresponding to a two-dimensional image showing an external appearance of the at least one object where the at least one object is displayed as from a position that is separate from the at least one object by a certain distance, and the method further comprising identifying the predetermined object by recognizing a figure of the predetermined object included in the two-dimensional image.

19. The data processing method according to claim 18, wherein extracting the predetermined three-dimensional data includes extracting position information along the direction perpendicular to the planar direction in the two-dimensional image corresponding to the position information of the predetermined object included in the two-dimensional image.

20. The data processing method according to claim 11, wherein identifying the predetermined object includes identifying the predetermined object based on the two-dimensional data and an estimation model that is trained to estimate a type of the predetermined object among the at least one object based on the two-dimensional data.

* * * * *